(12) United States Patent
Yoshitomo et al.

(10) Patent No.: US 9,522,868 B2
(45) Date of Patent: Dec. 20, 2016

(54) TETRAKIS(ETHER-SUBSTITUTED FORMYLPHENYL)

(71) Applicant: HONSHU CHEMICAL INDUSTRY CO., LTD., Tokyo (JP)

(72) Inventors: Akira Yoshitomo, Wakayama (JP); Tatsuya Iwai, Wakayama (JP)

(73) Assignee: HONSHU CHEMICAL INDUSTRY CO., LTD., Tokyo (JP)

( * ) Notice: Subject to any disclaimer, the term of this patent is extended or adjusted under 35 U.S.C. 154(b) by 0 days.

(21) Appl. No.: 14/868,233

(22) Filed: Sep. 28, 2015

(65) Prior Publication Data

US 2016/0016884 A1    Jan. 21, 2016

Related U.S. Application Data

(62) Division of application No. 13/000,191, filed as application No. PCT/JP2009/061289 on Jun. 22, 2009, now abandoned.

(30) Foreign Application Priority Data

Jun. 20, 2008 (JP) .................. 2008-162588
Jun. 20, 2008 (JP) .................. 2008-162606

(51) Int. Cl.
| C07C 69/76  | (2006.01) |
| C07C 69/738 | (2006.01) |
| C07C 39/17  | (2006.01) |
| C07C 47/57  | (2006.01) |
| C07C 59/70  | (2006.01) |
| C07C 69/712 | (2006.01) |

(52) U.S. Cl.
CPC ............. *C07C 69/738* (2013.01); *C07C 39/17* (2013.01); *C07C 47/57* (2013.01); *C07C 59/70* (2013.01); *C07C 69/712* (2013.01); *C07C 2101/14* (2013.01); *C07C 2103/74* (2013.01)

(58) Field of Classification Search
USPC .............................. 560/18, 53, 66
See application file for complete search history.

(56) References Cited

U.S. PATENT DOCUMENTS

| 8,043,789 B2 | 10/2011 | Lee et al. |
| 8,278,022 B2 * | 10/2012 | Mimura ............... G03F 7/0045 430/270.1 |

FOREIGN PATENT DOCUMENTS

| JP | 8193052 A | 7/1996 |
| JP | 2001312055 A | 11/2001 |
| JP | 2006267996 A | 10/2006 |
| JP | 200739381 A | 2/2007 |
| JP | 2007112777 A | 5/2007 |
| JP | 20081604 A | 1/2008 |
| WO | 2007034719 A1 | 3/2007 |
| WO | 2007142353 A1 | 12/2007 |
| WO | 2007148456 A1 | 12/2007 |

OTHER PUBLICATIONS

Declaration of Interference Issued by USPTO on Aug. 21, 2015 for U.S. Appl. No. 13/000,191.
Interference Decision mailed on Oct. 20, 2015, for a parent application (U.S. Appl. No. 13/000,191).

* cited by examiner

*Primary Examiner* — Pancham Bakshi
(74) *Attorney, Agent, or Firm* — Law Office of Katsuhiro Arai

(57) ABSTRACT

A tetrakis(ether-substituted formylphenyl) expressed by General Formula (1):

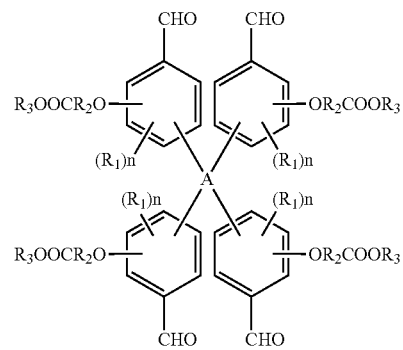

wherein $R_1$ represents an alkyl group with 1 to 8 carbon atoms or alkoxyl group with 1 to 8 carbon atoms, or aromatic hydrocarbon group or saturated hydrocarbon group with 1 to 8 carbon atoms having an aromatic hydrocarbon group, n represents 0 or an integer of 1 to 3, $R_2$ represents a divalent monocyclic or fused-ring aromatic hydrocarbon group with 6 to 15 carbon atoms or divalent aliphatic hydrocarbon group with 1 to 8 carbon atoms that may have a monocyclic or fused-ring aromatic hydrocarbon group with 6 to 15 carbon atoms, $R_3$ represents a hydrogen atom or alkyl group with 1 to 6 carbon atoms, A represents a tetravalent carbon atom group or tetravalent saturated hydrocarbon group with 2 or more carbon atoms, where, if A is a tetravalent saturated hydrocarbon group with 2 or more carbon atoms, the two carbon atoms in the A group are bonded with two phenyl groups, respectively.

1 Claim, No Drawings

TETRAKIS(ETHER-SUBSTITUTED FORMYLPHENYL)

CROSS-REFERENCE TO RELATED APPLICATIONS

This application is a divisional of U.S. patent application Ser. No. 13/000,191, filed Feb. 10, 2011, now abandoned, which is the U.S. National Phase under 35 U.S.C. §371 of International Application PCT/JP2009/061289, filed Jun. 22, 2009, which claims priority to Japanese Patent Application No. 2008-162588, filed Jun. 20, 2008, and Japanese Patent Application No. 2008-162606, filed Jun. 20, 2008, each disclosure of which is incorporated herein by reference in its entirety. The International Application was not published under PCT Article 21(2) in English.

TECHNICAL FIELD

The present invention relates to a new tetrakis(ether-substituted formylphenyl) and new polynuclear polyphenol derived therefrom, and more specifically to: a new tetrakis (ether-substituted formylphenyl) having four terminal phenyl groups in the molecule where the phenyl nucleus has the ether group and formyl group as nuclear substitution groups; a polynuclear polyphenol constituted by a compound of such tetrakis(ether-substituted formylphenyl) where each formyl group is further substituted by two phenol groups; and a polynuclear polyphenol having four terminal phenyl groups in the molecule where the phenyl nucleus has an oxycarbonyl hydrocarbon ether group with an acid-cleavable group bonded to it and the phenyl group is further bonded with a methyl group which is substituted by two phenol groups.

PRIOR ART

In recent years, certain materials such as epoxy resins, photosensitive resists, or the like for electronic components are seeing a need for further improvement in response to fine processing technology, etc., and new material compounds are required to meet the above need. Known examples of such compounds include several compounds of a polynuclear poly(ether-substituted formylphenyl) having the alkoxycarbonyl hydrocarbon ether substitution group or hydroxycarbonyl hydrocarbon ether substitution group as well as polynuclear polyphenol that can be derived from the polynuclear poly(ether-substituted formylphenyl) by causing the formyl group to react further with a phenol. In particular, the latter polynuclear polyphenol has the reactive alkoxycarbonyl hydrocarbon ether substitution group or hydroxycarbonyl hydrocarbon ether substitution group in the molecule, where the terminal phenyl nucleus of the molecule has the highly reactive hydroxyl group, and the selection of the terminal structure and center structure of the molecule is also relatively easy in terms of manufacturing of compounds, and therefore this polynuclear polyphenol is suitable as a material compound for materials used for the aforementioned purposes and there is a need to add diverse features and high functions to such compounds according to the required material characteristics.

Conventionally for the polynuclear(ether-substituted formylphenyl) having the alkoxycarbonyl hydrocarbon ether substitution group in the terminal formylphenyl group of the molecule, several compounds are known including, for example, a bis(formylphenyl) compound constituted by methylene bis-salicylaldehyde whose hydroxyl group is substituted by the alkoxycarbonylalkyl group (Patent Literature 1), and 1-[α-methyl-α-(3-formyl-4-methoxycarbonylmethoxy-5-methylphenyl)ethyl]-4-[α,α-bis(3-formyl-4-methoxycarbonylmethoxy-5-methylphenyl)ethyl]benzene and other tris(formylphenyl) compounds (Patent Literature 2).

However, no tetrakis(ether-substituted formylphenyl) is known where a same carbon atom in the saturated hydrocarbon group is bonded with four phenyl groups or each of two carbon atoms in the saturated hydrocarbon group is bonded with two phenyl groups, each phenyl group having alkoxycarbonyl hydrocarbon ether substitution group or hydroxycarbonyl hydrocarbon ether substitution group, and formyl group.

Also conventionally for the polynuclear polyphenol that can be derived by causing the formyl group in the aforementioned polynuclear(ether-substituted formylphenyl) to react further with a phenol, several compounds are known including bis[4-carboxymethoxy-3-{bis(alkyl-substituted 4-hydroxyphenyl)}methylphenyl]methane and other polynuclear polyphenol dicarboxylic acids as well as compounds produced by alkoxy-alkylating the carboxylic acid thereof (Patent Literature 3), 1-[α-methyl-α-{3-bis(2,5-dimethyl-4-hydroxyphenyl)methyl-4-carboxymethoxy-5-methylphenyl}ethyl]-4-[α,α-bis {3-bis(2,5-dimethyl-4-hydroxyphenyl)methyl-4-carboxymethoxy-5-methylphenyl}ethyl]benzene and other polynuclear polyphenol compounds (Patent Literature 2), etc.

However, the world is yet to know any such polynuclear polyphenol that can be derived by causing the formyl group in the above-mentioned tetrakis (formylphenol) to react further with a phenol, where the polynuclear polyphenol has the phenyl nucleus having four alkoxycarbonyl hydrocarbon ether substitution groups or hydroxycarbonyl hydrocarbon ether substitution groups in the molecule as well as eight terminal phenol groups in the molecule, or such polynuclear polyphenol where at least one of the hydroxycarbonyl hydrocarbon ether substitution groups is protected by an acid-cleavable group.

In addition, polymers produced by protecting with an acid-cleavable group a part of the hydroxyl groups of polymers such as polyhydroxy styrene, or compounds produced by introducing an acid-cleavable group into the hydroxyl group-containing low-weight molecules of polyvalent phenols, or the like, are conventionally being examined as material compounds for epoxy resins, photosensitive resists, or the like, for electronic components. For example, a polynuclear polyphenol compound having two to three acid-cleavable groups at specified locations in the molecule as well as two or more triphenyl methane skeletons having the phenolic hydroxyl group, and a resist composition using such polynuclear polyphenol compounds, are disclosed (Patent Literatures 4 and 5). However, any such known conventional compound, if used as a material compound for photosensitive resist, especially as a material compound for electron beam or EUV resists material, does not provide sufficient functions such as heat resistance, resolution, or the like and therefore material compounds offering greater heat resistance and resolution are required.

As explained above, the characteristics required of material compounds are becoming increasingly diverse and advanced. On the other hand, polynuclear polyphenol, whose phenyl nucleus has the highly reactive hydroxyl group and which allows for selection of various terminal and center structures of the molecule and which can also be manufactured relatively easily, is suitable as the aforementioned material compounds for photosensitive resists, etc., having acid-cleavable groups.

Also for the structure having high reactivity and heat resistance, compounds having a structure to meet the aforementioned requirement include: a tetrakis(ether-substituted formylphenyl) compound having a saturated hydrocarbon group as its center skeleton where a same carbon atom is bonded with four phenyl groups or each of two different carbon atoms is bonded with two phenyl groups, each phenyl group having alkoxycarbonyl hydrocarbon ether substitution group or hydroxycarbonyl hydrocarbon ether substitution group, and formyl group; a polynuclear polyphenol compound that can be derived from the aforementioned compound by causing the formyl group to further react with a phenol; and a polynuclear polyphenol compound having acid-cleavable groups as well as a saturated hydrocarbon group as the center skeleton to structurally provide particularly high reactivity and heat resistance, where a same carbon atom has four phenyl groups or each of two carbon atoms has two phenyl groups and each phenyl group has the hydroxycarbonyl hydrocarbon ether group, where a part or the whole is substituted by an acid-cleavable group and the carbon atom bonded to each phenyl nucleus is substituted further by two phenol groups. The present invention was completed based on the discovery that such compounds are new.

Patent Literature 1: Japanese Patent Laid-open No. 2007-039381

Patent Literature 2: International Patent Application Publication No. 2007/142353

Patent Literature 3: Japanese Patent Laid-open No. 2007-112777

Patent Literature 4: International Patent Application Publication No. 2007/34719

Patent Literature 5: International Patent Application Publication No. 2007/148456

SUMMARY OF THE INVENTION

Problems to be Solved by the Invention

The present invention was developed in light of the aforementioned situation surrounding conventional polynuclear poly(ether-substituted formylphenyl) compounds and polynuclear polyphenol compounds, and it is the object of the present invention to provide: a tetrakis(ether-substituted formylphenyl) having a saturated hydrocarbon group as the center skeleton to structurally provide high reactivity and heat resistance where a same carbon atoms is bonded with four phenyl groups or each of two different carbon atoms is bonded with two phenyl groups, each phenyl group having alkoxycarbonyl hydrocarbon ether substitution group or hydroxycarbonyl hydrocarbon ether substitution group, and formyl group; a polynuclear polyphenol that can be derived from the tetrakis(ether-substituted formylphenyl) by causing the formyl group to react further with a phenol; and a polynuclear polyphenol where at least one of the aforementioned hydroxycarbonyl hydrocarbon ether substitution groups is protected by an acid-cleavable group.

Means for Solving the Problems

A new tetrakis(ether-substituted formylphenyl) and polynuclear polyphenol conforming to the present invention are expressed by General Formulas (1) and (2) below as well as General Formula (5) below.

[Chemical 1]

General Formula (1)

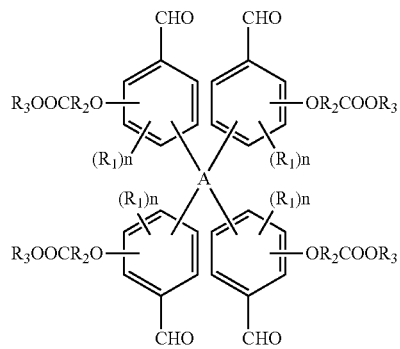

(In the formula, $R_1$ represents an alkyl group with 1 to 8 carbon atoms or alkoxyl group with 1 to 8 carbon atoms, or aromatic hydrocarbon group or saturated hydrocarbon group with 1 to 8 carbon atoms having an aromatic hydrocarbon group, n represents 0 or an integer of 1 to 3, $R_2$ represents a divalent monocyclic or fused-ring aromatic hydrocarbon group with 6 to 15 carbon atoms or divalent aliphatic hydrocarbon group with 1 to 8 carbon atoms that may have a monocyclic or fused-ring aromatic hydrocarbon group with 6 to 15 carbon atoms, $R_3$ represents a hydrogen atom or alkyl group with 1 to 6 carbon atoms, A represents a tetravalent carbon atom group or tetravalent saturated hydrocarbon group with 2 to 50 carbon atoms, where, if A is a tetravalent saturated hydrocarbon group with 2 to 50 carbon atoms, the two carbon atoms in the A group are bonded with two phenyl groups, respectively)

[Chemical 2]

General Formula (2)

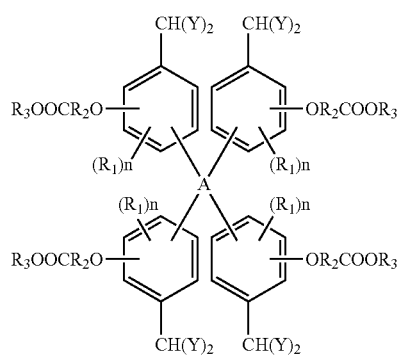

(In the formula, $R_1$, n, $R_2$, $R_3$ and A are the same as the corresponding items in General Formula (1) above, while Y represents a hydroxyphenyl group expressed by General Formula (3) below)

[Chemical 3]

General Formula (3)

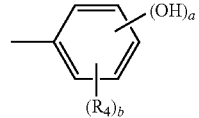

(In the formula, $R_4$ represents an alkyl group with 1 to 8 carbon atoms or alkoxyl group with 1 to 8 carbon atoms, or aromatic hydrocarbon group or saturated hydrocarbon group with 1 to 8 carbon atoms having an aromatic hydrocarbon group, a represents an integer of 1 to 3, and b represents 0 or an integer of 1 to 4, where, $1 \leq a+b \leq 5$ and if b is 2 or greater, $R_4$ may be the same or different.)

It should be noted that a polynuclear polyphenol where General Formula (3) above is represented by General Formula (4) below is a favorable embodiment of the present invention.

[Chemical 4]

General Formula (4)

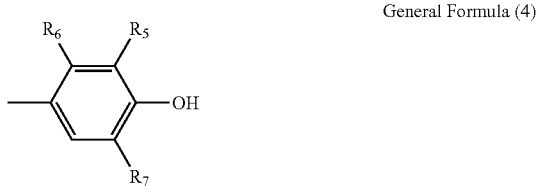

(In the formula, $R_5$, $R_6$ and $R_7$ respectively represent independently a hydrogen atom or alkyl group with 1 to 8 carbon atoms or alkoxyl group with 1 to 8 carbon atoms or aromatic hydrocarbon group or saturated hydrocarbon group with 1 to 8 carbon atoms having an aromatic hydrocarbon group)

[Chemical 5]

General Formula (5)

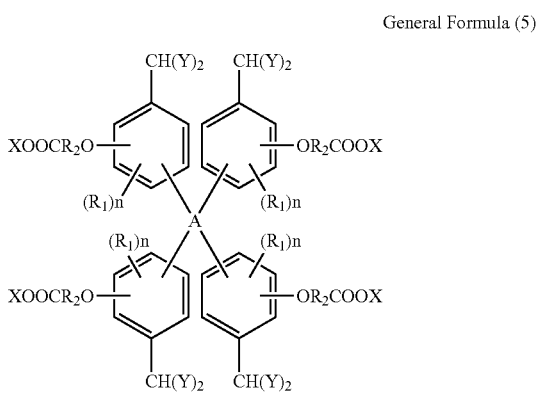

(In the formula, $R_1$, n, $R_2$ and A are the same as the corresponding items in General Formula (1) above, while X represents a hydrogen atom or acid-cleavable group expressed by General Formula (6) below, where in the formula, all four X's are not a hydrogen atom at the same time, and Y is the same as the corresponding item in General Formula (2) above)

[Chemical 6]

General Formula (6)

(In the formula, $R_{15}$ represents an alkylene group with 1 to 8 carbon atoms, $R_{16}$ represents a saturated hydrocarbon group with 1 to 30 carbon atoms, and h represents 0 or 1, where, if h is 1, $R_{16}$ represents a tertiary saturated hydrocarbon group with 4 to 30 carbon atoms.)

Effects of the Invention

A tetrakis(ether-substituted formylphenyl) expressed by General Formula (1) according to the present invention has four benzene rings in the molecule and each benzene ring has the highly reactive ester group- or carboxyl group-modified ether group and formyl group, and therefore it is useful as a material for reformers for phenol resins or the like, and photoresists, as an intermediate material for polynuclear polyphenol compounds that can be used as resist materials, etc., after reacting with a phenol, etc., and also as a reactive intermediate material, etc., for polynuclear aromatic compounds, etc., offering excellent heat resistance.

If used for phenol resins, epoxy resins, etc., such tetrakis (ether-substituted formylphenyl) is expected to demonstrate improved heat resistance (high glass transition temperature), flexibility, or water resistance.

The second new compound proposed by the present invention, or specifically a polynuclear polyphenol expressed by General Formula (2), has four triphenyl methane skeletons in the molecule and therefore offers high glass transition temperature and excellent heat resistance. In addition, the presence of four highly reactive carboxyl groups or ester groups and at least eight phenolic hydroxyl groups in the molecule should also improve the rate of alkali dissolution. Furthermore, due to selective reactivity and interaction of the hydroxyl group, carboxyl group or ester group, if used as a photosensitive resist or material thereof, this polynuclear polyphenol is expected to demonstrate excellent effects such as improved heat resistance and resolution of resist.

Moreover, the third new compound, or specifically a polynuclear polyphenol expressed by General Formula (5) according to the present invention, is a compound produced using a highly heat-resistant polynuclear polyphenol expressed by General Formula (2) as a material and protecting the carboxyl group with an acid-cleavable group, which means that if used as a resist material, this polynuclear polyphenol is expected to demonstrate excellent benefits toward improvement of heat resistance and resolution of resist. If used for phenol resins, epoxy resins, etc., such polynuclear polyphenol will likely achieve improved heat resistance (high glass transition temperature), flexibility and water resistance.

BEST MODE FOR CARRYING OUT THE INVENTION

With respect to General Formula (1) above, in the formula, specific examples of the alkyl group with 1 to 8 carbon atoms represented by $R_1$ include the methyl group, ethyl group, propyl group, butyl group, t-butyl group, pentyl group, 3-methylpentyl group, cyclopropyl group, cyclopentyl group, 3-methylcyclopentyl group, cyclohexyl group, 2,4-dimethylcyclohexyl group, cycloheptyl group and other straight-chain, branched-chain or cyclic saturated hydrocarbon groups. Examples of the alkoxy group with 1 to 8 carbon atoms include the methoxy group, ethoxy group, propoxy group, isopropoxy group, butoxy group, t-butoxy group, pentyloxy group, isopentyloxy group, cyclopropoxy group, cyclopentyloxy group, 3-methylcyclopentyloxy group, cyclohexyloxy group, 2,4-dimethylcyclohexyloxy group, cycloheptyloxy group and other straight-chain, branched-chain or cyclic alkoxy groups. Of these, a straight-chain or branched-chain alkyl group or alkoxy group with 1 to 4 carbon atoms or cyclic alkyl group or cyclic alkoxy group with 5 to 7 carbon atoms is preferable, but a straight-chain or branched-chain alkyl group with 1 to 4 carbon atoms is more preferable. Also, n is preferably 1.

As for the aromatic hydrocarbon group or alkyl group with 1 to 8 carbon atoms having an aromatic hydrocarbon group, as represented by $R_1$, the aromatic hydrocarbon group need not be substituted by the alkyl group and specific examples include the phenyl group, 4-methylphenyl group, etc., where the total number of carbon atoms of substitution alkyl groups is preferably 1 to 8. The alkyl group with 1 to 8 carbon atoms having an aromatic hydrocarbon group is such that an aromatic hydrocarbon group substitutes the side chain or main chain of an alkyl group with 1 to 8 carbon atoms, where specific examples include the benzyl group, 1-phenylethyl group, and (4-methylphenyl)methyl group.

Regarding General Formula (1) above, $R_2$ in the alkoxycarbonyl hydrocarbon ether group in the formula represents a divalent monocyclic or fused-ring aromatic hydrocarbon group with 6 to 15 carbon atoms or divalent aliphatic hydrocarbon group with 1 to 8 carbon atoms that may have a monocyclic or fused-ring aromatic hydrocarbon group with 6 to 15 carbon atoms, where the monocyclic or fused-ring aromatic hydrocarbon group with 6 to 15 carbon atoms has preferably 6 to 10 carbon atoms, and this aromatic hydrocarbon group may be substituted by an alkyl group with 1 to 4 carbon atoms, and specific preferred examples of $R_2$ include 1,2-phenylene, 1,3-phenylene, 1,4-phenylene, 2-methyl-1,4-phenylene, 2,6-dimethyl-1,4-phenylene, 2-isopropyl-1,4-phenylene and other monocyclic aromatic hydrocarbon groups, as well as 1,5-naphthylene, 2,7-naphthylene, anthracene-2,7-diyl and other fused-ring aromatic hydrocarbon groups.

Also regarding the divalent aliphatic hydrocarbon group with 1 to 8 carbon atoms that may have a monocyclic or fused-ring aromatic hydrocarbon group with 6 to 15 carbon atoms represented by $R_2$ above, one embodiment which is a divalent aliphatic hydrocarbon group with 1 to 8 carbon atoms that does not have the aforementioned aromatic hydrocarbon group is a straight-chain, branched-chain or cyclic saturated or unsaturated hydrocarbon group with 1 to 8 carbon atoms, where specific examples include methylene, ethylene, ethane-1,1-diyl, propylene, propan-1,1-diyl, butylene, ethylethylene, 2-methyl-1,3-propylene, 2-methyl butane-1,4-diyl, pentamethylene, hexamethylene, 1,1,2,2-tetramethylethylene, isopropylmethylene, 1,1-diethyl-methylene, cyclopentane-1,3-diyl, cyclohexane-1,4-diyl and other alkylene groups, as well as vinylene, propenylene, 2-butenylene, 2-pentenylene and other alkenylene groups.

Also with regard to the divalent aliphatic hydrocarbon group with 1 to 8 carbon atoms that may have a monocyclic or fused-ring aromatic hydrocarbon group with 6 to 15 carbon atoms represented by $R_2$ above, another embodiment which is an aliphatic hydrocarbon group that has an aromatic hydrocarbon group may be an aliphatic hydrocarbon group having an aromatic hydrocarbon group in the side chain or aliphatic hydrocarbon group having an aromatic hydrocarbon group in the main chain. Preferably it is a divalent aliphatic hydrocarbon group with 1 to 8 carbon atoms that has a monocyclic or fused-ring aromatic hydrocarbon group in the main chain, where the —$R_2COOR_3$ group is expressed by General Formula (7) below.

[Chemical 7]

—$(R_8)c$-$(R_9)d$-$(R_{10})e$-$COOR_3$    General Formula (7)

In the formula, $R_8$ and $R_{10}$ respectively represent independently an aliphatic hydrocarbon group with 1 to 8 carbon atoms, c and e are 1 or 0, and d is 1, where, however, the total number of carbon atoms of $R_8+R_{10}$ is 1 to 8 and c and e are not both 0 at the same time, and $R_9$ represents a monocyclic or fused-ring aromatic hydrocarbon group with 6 to 15 carbon atoms. Note that the monocyclic or fused-ring aromatic hydrocarbon group with 6 to 15 carbon atoms as represented by $R_9$ is the same as the monocyclic or fused-ring aromatic hydrocarbon group when $R_2$ is a monocyclic or fused-ring aromatic hydrocarbon group with 6 to 15 carbon atoms, while the aliphatic hydrocarbon group with 1 to 8 carbon atoms as represented by $R_8$ or $R_{10}$ is the same as the divalent aliphatic hydrocarbon group with 1 to 8 carbon atoms that does not have an aromatic hydrocarbon group of $R_2$.

Of these, the aromatic hydrocarbon group of $R_9$ is preferably a phenylene group or naphthylene group, while the aliphatic hydrocarbon group of $R_8$ or $R_{10}$ is preferably an alkylene group with 1 to 4 carbon atoms.

Accordingly, specific examples of the divalent aliphatic hydrocarbon group with 1 to 8 carbon atoms having a monocyclic or fused-ring aromatic hydrocarbon group with 6 to 15 carbon atoms include those expressed as follows.

[Chemical 8]

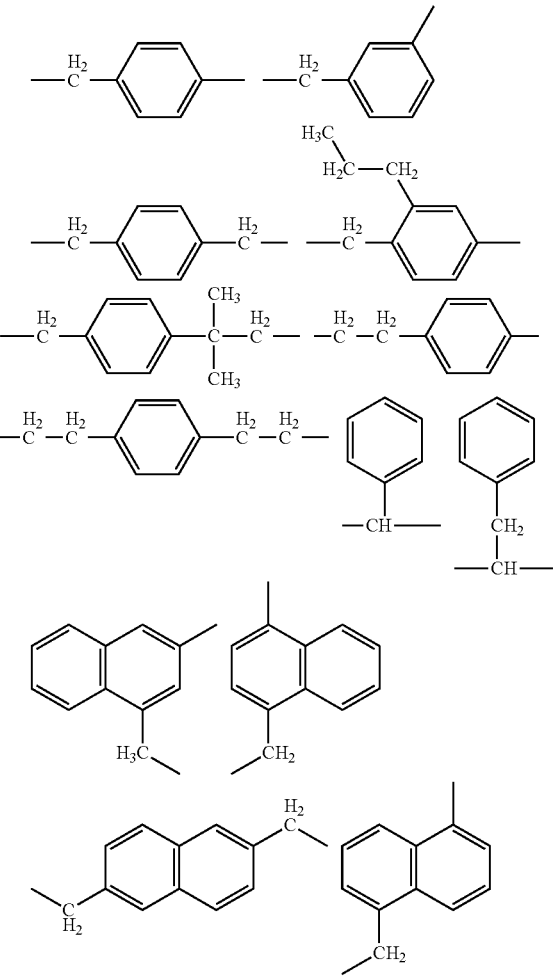

Also for $R_2$ in General Formula (1), a primary or secondary carbon atom is preferable for the reason that any carbon atom bonded with an ether group which in turn is bonded with an aromatic nucleus is stable in the presence of acids.

Under the present invention, $R_2$ is preferably a straight-chain or branched-chain saturated or unsaturated hydrocarbon group with 1 to 8 carbon atoms, or more preferably be such a hydrocarbon group with 1 to 4 carbon atoms.

On the other hand, $R_3$ represents a hydrogen atom or alkyl group with 1 to 6 carbon atoms, where the alkyl group with 1 to 6 carbon atoms is a straight-chain or branched-chain or cyclic alkyl group, or specifically methyl, ethyl, n-butyl, t-butyl, sec-butyl, isopropyl, n-propyl, cyclohexyl, etc., for example.

Under the present invention, $R_3$ is preferably a hydrogen atom, primary alkyl group or secondary alkyl group, and a particularly preferred form of the alkyl group is a straight-chain or branched-chain alkyl group with 1 to 4 carbon atoms.

Accordingly with respect to the tetrakis(ether-substituted formylphenyl) expressed by General Formula (1), specific examples of the ester-substituted hydrocarbon group bonded with the ether group, or to be more specific the carboxy hydrocarbon group or alkoxycarbonyl hydrocarbon group represented by —$R_2COOR_3$, include the carboxymethyl group, methoxycarbonylmethyl group, carboxypropyl group, ethoxycarbonylpropyl group, 3-methoxycarbonyl-2-methyl-1-propyl group, methoxycarbonylpropyl group and those expressed as follows.

[Chemical 9]

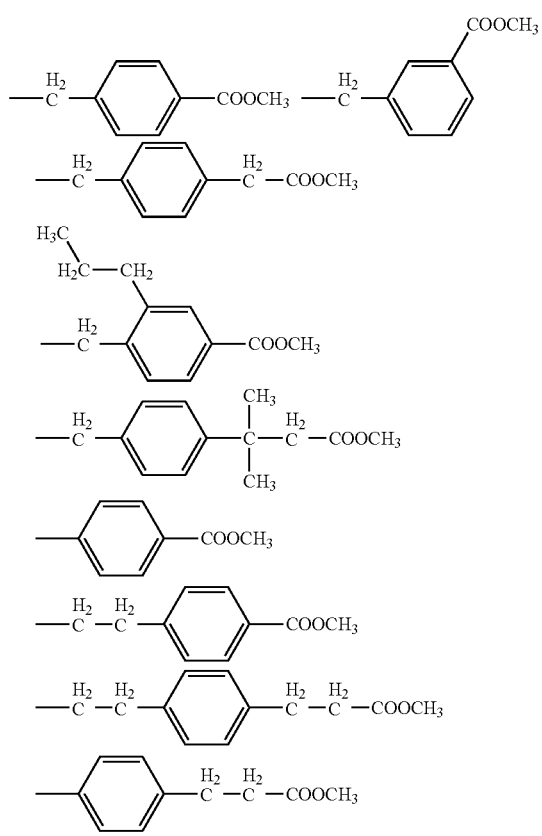

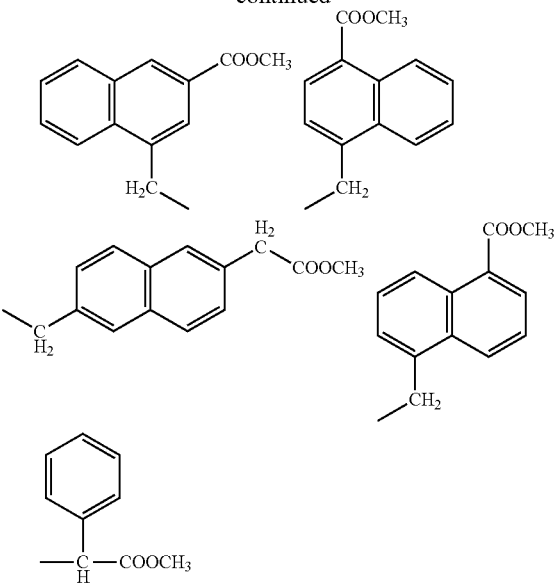

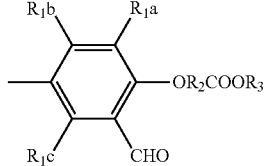

Of these, a more preferred form of the —$R_2COOR_3$ group is the carboxymethyl group or methoxycarbonylmethyl group.

Also, a preferred form of the ether-substituted formylphenyl group in General Formula (1) is represented by General Formula (8) below.

[Chemical 10]

General Formula (8)

(In the formula, $R_1a$, $R_1b$ and $R_1c$ are the same as $R_1$ in General Formula (1).)

Also note that in General Formula (8), $R_1a$ is preferably an alkyl group, while $R_1b$ and $R_1c$ are preferably both a hydrogen atom.

In General Formula (1), A represents a tetravalent carbon atom group or tetravalent saturated hydrocarbon group with 2 to 50 carbon atoms having two divalent carbon atoms, or preferably a saturated hydrocarbon group with 2 to 30 carbon atoms, where the saturated hydrocarbon group may be a straight-chain or branched-chain saturated hydrocarbon group, monocyclic aliphatic saturated hydrocarbon group or polycyclic aliphatic saturated hydrocarbon group, bridged cyclic aliphatic saturated hydrocarbon group or terpene saturated hydrocarbon group, all of which may have a substitution group, or a saturated hydrocarbon group containing both a chained variation and cyclic variation thereof, etc. Of these, those expressed below are preferred forms of the saturated hydrocarbon group, for example.

[Chemical 11]

Formula 5

Formula 10

[Chemical 12]

General Formula (9)

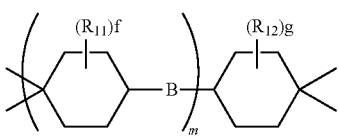

(In the formula, $R_{11}$ and $R_{12}$ respectively represent independently an alkyl group with 1 to 8 carbon atoms, f and g respectively represent independently 0 or an integer of 1 to 4, B represents a single bond or divalent saturated hydrocarbon group with 1 to 10 carbon atoms, and m represents 0 or 1. The divalent saturated hydrocarbon group is a straight-chain alkylene group with 1 to 10 carbon atoms or branched-chain or cyclic alkylene group with 3 to 10 carbon atoms.)

In the saturated hydrocarbon group expressed by General Formula (9) above, preferred examples of the tetravalent saturated hydrocarbon group include those shown below.

[Chemical 13]

Formula

Formula

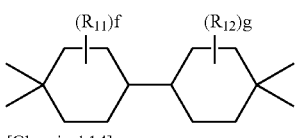

[Chemical 14]

General Formula (10)

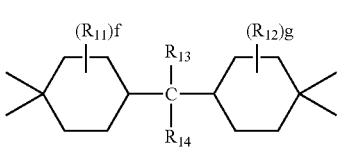

(In the formula, $R_{11}$, $R_{12}$, f and g are the same as the corresponding items in General Formula (9), while $R_{13}$ and $R_{14}$ respectively represent independently a hydrogen atom or alkyl group with 1 to 9 carbon atoms. Note, however, that the total number of carbon atoms of $R_{13}+R_{14}$ is 9 or less. Also, the alkyl group with 1 to 9 carbon atoms is a straight-chain alkyl group with 1 to 9 carbon atoms or branched-chain or cyclic alkyl group with 3 to 10 carbon atoms.)

It is preferable that at least one of $R_{13}$ and $R_{14}$ is, or both are, a hydrogen atom, primary alkyl group or secondary alkyl group, or in particular a chained or branched alkyl group. The carbon number of $R_{13}$ and $R_{14}$ is preferably 1 to 4.

With regard to the saturated hydrocarbon group expressed by General Formula (10), preferred examples of the tetravalent saturated hydrocarbon group include those shown below.

[Chemical 15]

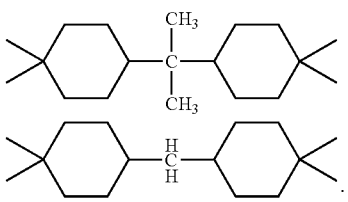

Accordingly, specific examples of the tetrakis(ether-substituted formylphenyl) expressed by General Formula (1) above include:

2,2-bis {4,4-bis(3-formyl-4-methoxycarbonylmethoxy-5-methylphenyl)cyclohexyl}propane,

[Chemical 16]

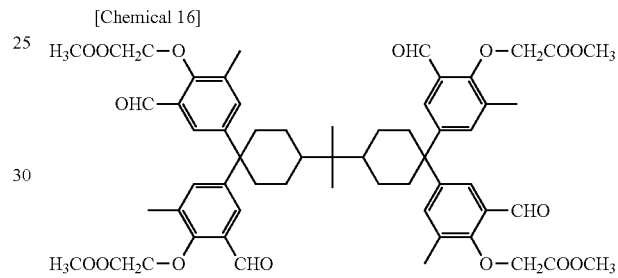

1,1,4,4-tetrakis(3-formyl-4-methoxycarbonylmethoxy-5-methylphenyl)cyclohexane, 4,4,4',4'-tetrakis(3-formyl-4-methoxycarbonylmethoxy-5-methylphenyl)-1,1'-bicyclohexane,
bis{4,4-bis(3-formyl-4-methoxycarbonylmethoxy-5-methylphenyl)cyclohexyl}methane,
2,2-bis[4,4-bis {3-formyl-4-(4-methoxycarbonylphenyl)methoxy-5-methylphenyl}cyclohexyl]propane,
2,2-bis {4,4-bis(4-carboxymethoxy-3-formyl-5-methylphenyl)cyclohexyl}propane,

[Chemical 17]

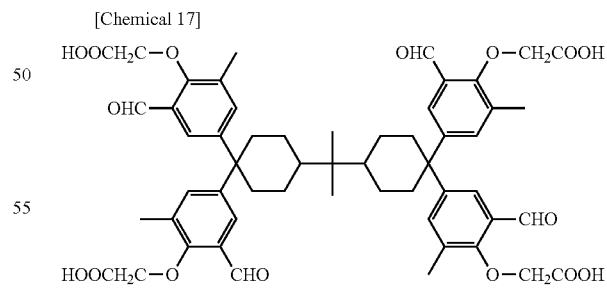

1,1,4,4-tetrakis(4-carboxymethoxy-3-formyl-5-methylphenyl)cyclohexane,
4,4,4',4'-tetrakis(4-carboxymethoxy-3-formyl-5-methylphenyl)-1,1'-bicyclohexane,
bis {4,4-bis(4-carboxymethoxy-3-formyl-5-methylphenyl) cyclohexyl}methane, and
2,2-bis[4,4-bis {4-(4-carboxyphenyl)methoxy-3-formyl-5-methylphenyl}cyclohexyl]propane, among others.

The manufacturing method of such tetrakis(ether-substituted formylphenyl) expressed by General Formula (1) above conforming to the present invention is not limited in any way, and it can be obtained by, for example, a method similar to the one described in WO2007/142353. For instance, in the case of one such tetrakis(ether-substituted formylphenyl) based on 2,2-bis{4,4-bis(3-formyl-4-methoxycarbonylmethoxy-5-methylphenyl)cyclohexyl}propane, as shown in Reaction Formula (1) below, the tetrakis(hydroxymethylphenol) expressed by the formula below, which corresponds to the target tetrakis(ether-substituted formylphenyl) compound, is reacted with hexamethylenetetramine in the presence of an acid, and then the reaction product is hydrolyzed to obtain the tetrakis(formyl-hydroxyphenyl) expressed by the formula below. By using this tetrakis(formyl-hydroxyphenyl) as the direct material and reacting it with methylchloroacetate, for example, in the presence of a base, as shown in Reaction Formula (2) below, the target tetrakis(ether-substituted formylphenyl) can be obtained. Obtaining a hydroxycarbonyl hydrocarbon ether substitution product can be achieved by, for example, hydrolyzing the aforementioned alkoxycarbonyl hydrocarbon group into a hydroxycarbonyl hydrocarbon group according to Reaction Formula (3).

Reaction Formula (1)

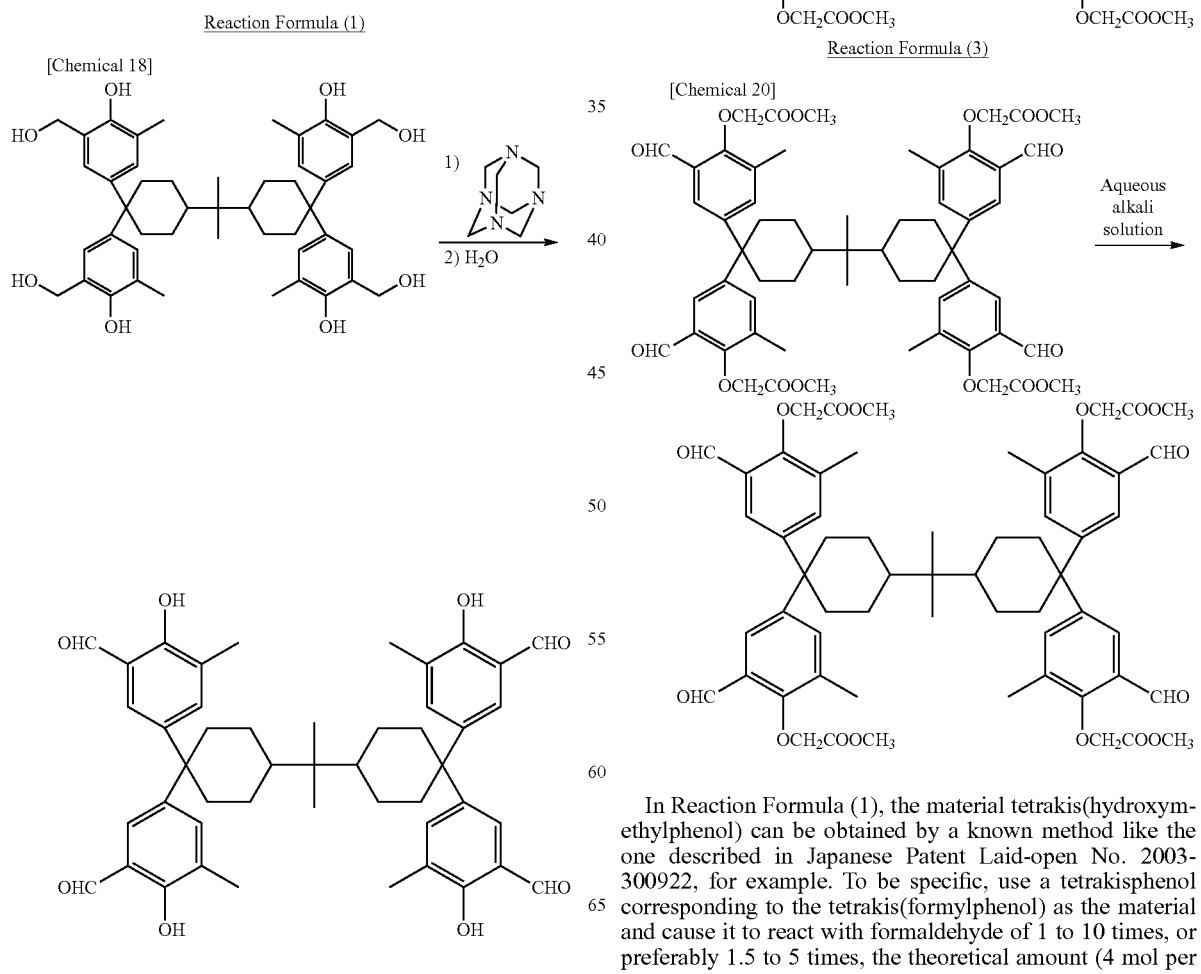

Reaction Formula (2)

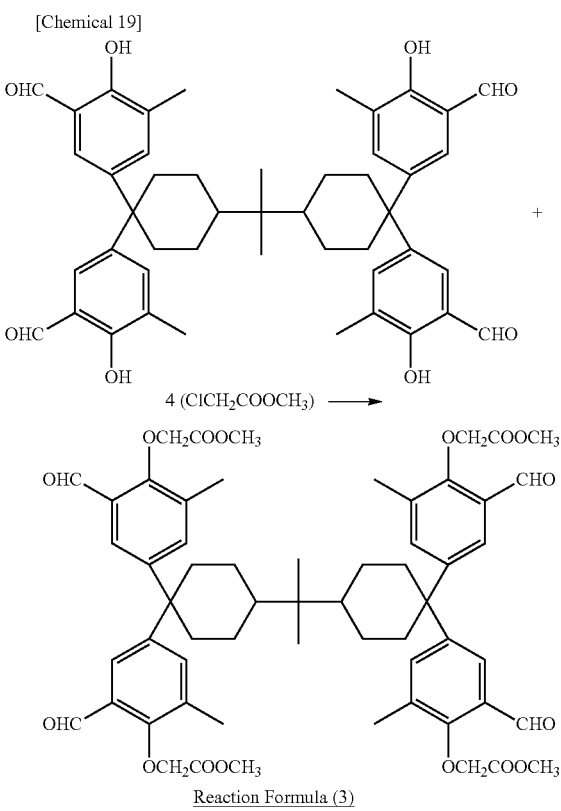

In Reaction Formula (1), the material tetrakis(hydroxymethylphenol) can be obtained by a known method like the one described in Japanese Patent Laid-open No. 2003-300922, for example. To be specific, use a tetrakisphenol corresponding to the tetrakis(formylphenol) as the material and cause it to react with formaldehyde of 1 to 10 times, or preferably 1.5 to 5 times, the theoretical amount (4 mol per 1 mol of tetrakis phenol) in the presence of a base in water or a mixed solvent comprising water and organic solvent, and then neutralize the obtained reaction product. Under the method to obtain a tetrakis(formylphenol) from a tetrakis (hydroxymethylphenol) as illustrated by Reaction Formula (1) above, any known method can be used like the one described in WO2007/139191, for example. To be specific, as exemplified in Reaction Formula (1), it can be obtained by using as the material the tetrakis(hydroxymethylphenol) obtained above which corresponds to the tetrakis(formyl phenol), causing it to react with hexamethylenetetramine in the presence of an acid, and then hydrolyzing the reaction product.

A tetrakis(ether-substituted formylphenyl) conforming to the present invention can be obtained by using as the direct material a tetrakis(formyl phenol) obtained above which corresponds to the target tetrakis(ether-substituted formylphenyl), and causing it to react with halogenated alkoxycarbonyl hydrocarbon expressed by General Formula (11) below in the presence of a base in a solvent as illustrated by Reaction Formula (2), for example.

[Chemical 21]

Z—R$_2$COOR$_3$  General Formula (11)

In the formula, Z represents a halogen atom, while R$_2$ and R$_3$ are the same as the corresponding items in General Formula (1).

Note that for the halogen atom, the chlorine atom or bromine atom is preferred.

To be specific, the halogenated alkoxycarbonyl hydrocarbon expressed by General Formula (11) above is preferably methylchloroacetate, methylbromoacetate, methyl p-chloromethyl benzoate, methyl p-bromobenzoate, etc., for example.

For the base to be used, either an organic base or inorganic base can be used. Preferred examples of the organic base include tetramethylammonium hydroxide and other hydroxy quaternary amines, and 1,8-diazabicyclo[5.4.0]undec-7-ene (abbreviated as "DBU"), among others.

On the other hand, preferred examples of the inorganic base include sodium hydroxide and other alkali metal hydroxides, potassium carbonate, sodium carbonate and other alkali metal carbonates, sodium hydride, potassium hydride, lithium hydride and other alkali metal hydrides, and t-butoxy potassium and other alkoxy alkali metals, among others.

Any such base is added normally by an amount in a range of 4 mol to 8 mol per 1 mol of the tetrakis(formylhydroxyphenyl) illustrated by Reaction Formula (2) above.

The solvent used in the reaction is preferably dioxane, THF or other ether, dimethylformamide, dimethylacetoamide or other amide, dimethylsulfoxide, hexamethylene phosphonic acid amide, pyridine, 4-methylpyridine, N-methylpyrrolidone or other amine, etc., or any mixture thereof.

The amount of solvent used is normally in a range of 1 part by weight to 10 parts by weight, or preferably in a range of 2 to 5 parts by weight, per 1 part by weight of the material tetrakis(formyl-hydroxyphenyl) from the viewpoint of reaction volume ratio, etc.

If necessary, potassium iodide or other alkali metal iodide, copper, copper chloride or other copper compound, tetrabutylammonium bromide or other phase transfer catalyst, or any other reaction accelerator additive, can be added to accelerate the etherification reaction. Although the method and order of introducing the reaction materials are not limited, normally it is preferable to mix together the material tetrakis(formyl-hydroxyphenyl) and base to produce an oxy salt, and then add to this liquid mixture the alkoxycarbonyl hydrocarbon salt expressed by General Formula (11).

The reaction can be implemented at temperatures normally in a range of 20° C. to 150° C., or preferably in a range of 50° C. to 80° C., for several hours, such as 2 to 20 hours. The reaction pressure is normally in a range of slight decompression to slight compression, or preferably around normal pressure.

After the reaction is complete, an organic solvent such as toluene or cyclohexane, etc., is added to the reaction mixture as deemed appropriate, along with water, to wash the mixture to remove the water layer, after which water is added to the oil layer, if necessary, followed by agitation and washing to remove the solvent by distillation from the oil layer, to obtain the target tetrakis(ether-substituted formylphenyl) conforming to the present invention as expressed by General Formula (1).

If the target tetrakis(ether-substituted formylphenyl) must have higher purity, add a solvent such as hexane or other aliphatic saturated hydrocarbon, methanol or other aliphatic lower alcohol, toluene or other aromatic hydrocarbon, or methylethylketone or other aliphatic ketone, to dissolve the obtained tetrakis(ether-substituted formylphenyl) and then cause crystallization or precipitation and filter out the precipitated target, or isolate and refine tetrakis(ether-substituted formylphenyl) by means of column chromatography.

Also with respect to the tetrakis(ether-substituted formylphenyl) expressed by General Formula (1), the manufacturing method to obtain a carboxy hydrocarbon oxy substitution product of the ether group when R$_3$ is a hydrogen atom is not limited in any way. However, such a carboxy hydrocarbon group (—R$_2$COOH) substitution product can be obtained easily as illustrated by Reaction Formula (3) by hydrolyzing the alkoxycarbonyl hydrocarbon group (—R$_2$COOR$_3$) substitution product where R$_3$ is a primary alkyl group, which constitutes the obtained tetrakis(ether-substituted formylphenyl), in a solvent in the presence of an alkali.

For the aqueous alkali solution used in the hydrolysis reaction, sodium hydroxide, potassium hydroxide or other strong inorganic aqueous alkali solution, or tetramethylammonium hydroxide or other strong organic aqueous alkali solution, is preferred, where the alkali concentration is in a range of 5 to 50%, or preferably in a range of 10 to 30%. The amount of alkali used is normally in a range of 4 mol to 16 mol, or preferably in a range of 8 mol to 12 mol, per 1 mol of the material alkoxycarbonyl hydrocarbon group substitution product. The reaction temperature is normally in a range of 0 to 100° C., or preferably in a range of 20 to 60° C. Under these reaction conditions, the reaction normally ends in 2 to 20 hours or so.

After the reaction is complete, the reaction product is refined according to any known method such as neutralization by adding an acid to the reaction liquid, or if necessary, a target of higher purity can be obtained.

Next, the second new compound proposed by the present invention, or specifically a polynuclear polyphenol derived from the aforementioned tetrakis(ether-substituted formylphenyl), is expressed by General Formula (2) below.

[Chemical 22]

General Formula (2)

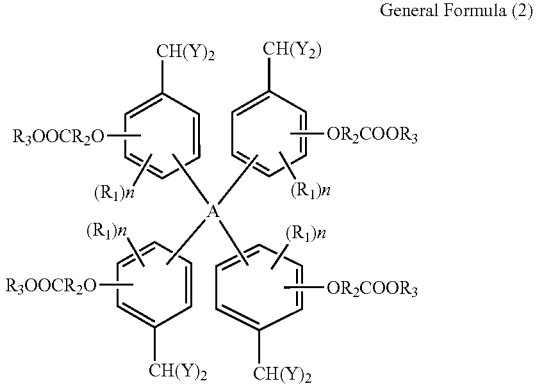

(In the formula, $R_1$, n, $R_2$, $R_3$ and A are the same as the corresponding items in General Formula (1) above, while Y represents a hydroxyphenyl group expressed by General Formula (3) below)

[Chemical 23]

General Formula (3)

(In the formula, $R_4$ represents an alkyl group with 1 to 8 carbon atoms or alkoxyl group with 1 to 8 carbon atoms, or aromatic hydrocarbon group or saturated hydrocarbon group with 1 to 8 carbon atoms having an aromatic hydrocarbon group, a represents an integer of 1 to 3, and b represents 0 or an integer of 1 to 4, where $1 \leq a+b \leq 5$ and if b is 2 or greater, $R_4$ may be the same or different.)

Note that in a preferred case, General Formula (3) above is represented by General Formula (4) below.

[Chemical 24]

General Formula (4)

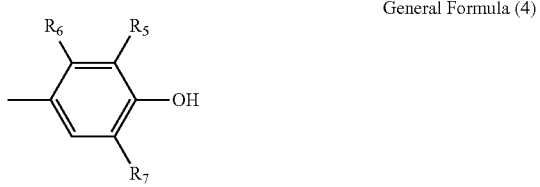

(In the formula, $R_5$, $R_6$ and $R_7$ respectively represent independently a hydrogen atom or alkyl group with 1 to 8 carbon atoms or alkoxyl group with 1 to 8 carbon atoms or aromatic hydrocarbon group or saturated hydrocarbon group with 1 to 8 carbon atoms having an aromatic hydrocarbon group.)

In General Formula (2), the tetravalent saturated hydrocarbon group with 2 to 50 carbon atoms as represented by A is specifically the same as A in General Formula (1), where a preferred number of carbon atoms is 2 to 30. A is preferably a saturated hydrocarbon group expressed by Chemical 11 or General Formula (9) above, or more preferably be a saturated hydrocarbon group expressed by Chemical 13 or General Formula (10) above.

For the alkyl group, alkoxyl group or aromatic hydrocarbon group or saturated hydrocarbon group with 1 to 8 carbon atoms having an aromatic hydrocarbon group as represented by $R_4$ or any one of $R_5$ to $R_7$, specifically it is the same as the alkyl group, alkoxyl group or aromatic hydrocarbon group or saturated hydrocarbon group with 1 to 8 carbon atoms having an aromatic hydrocarbon group as represented by $R_1$. The alkyl group is preferably a straight-chain or branched-chain alkyl group with 1 to 4 carbon atoms or cycloalkyl group with 5 to 7 carbon atoms, while the alkoxyl group is preferably an alkoxyl group with 1 to 4 carbon atoms or cycloalkoxyl group with 5 to 7 carbon atoms, while the aromatic hydrocarbon is preferably a phenyl group.

If b=4, or $R_4$ is substituted in four positions in General Formula (3), a substitution group that can bond with the formyl group in the o-position relative to the hydroxyl group is preferred in terms of synthesis.

To be specific, therefore, examples of the substitution phenyl group expressed by General Formula (3) or General Formula (4) above include, as those having one hydroxyl group (a is 1): 4-hydroxyphenyl group, 3-methyl-4-hydroxyphenyl group, 2-methyl-4-hydroxyphenyl group, 3,6-dimethyl-4-hydroxyphenyl group, 2,5-dimethyl-4-hydroxyphenyl group, 3,5-dimethyl-4-hydroxyphenyl group, 2,3,5-trimethyl-4-hydroxyphenyl group, 3-ethyl-4-hydroxyphenyl group, 3-isopropyl-4-hydroxyphenyl group, 3-t-butyl-4-hydroxyphenyl group, 3-t-butyl-6-methyl-4-hydroxyphenyl group, 3,5-di-t-butyl-4-hydroxyphenyl group, 3-sec-butyl-4-hydroxyphenyl group, 3-t-octyl-4-hydroxyphenyl group, 3-t-butyl-5-methyl-4-hydroxyphenyl group, 2-cyclohexyl-4-hydroxyphenyl group, 3-cyclohexyl-4-hydroxyphenyl group, 2-cyclohexyl-5-methyl-4-hydroxyphenyl group, 2-methyl-5-cyclohexyl-4-hydroxyphenyl group, 5-methyl-2-hydroxyphenyl group, 4,6-dimethyl-2-hydroxyphenyl group, 3,4,6-trimethyl-2-hydroxyphenyl group, 3,5-di-t-butyl-2-hydroxyphenyl group, 5-t-octyl-2-hydroxyphenyl group, 3-methoxy-4-hydroxyphenyl group, 5-methoxy-4-hydroxyphenyl group, 3-n-hexyl oxy-4-hydroxyphenyl group, 3-n-octyloxy-4-hydroxyphenyl group, 5-butoxy-2-hydroxyphenyl group, 3-phenyl-4-hydroxyphenyl group, 3-methyl-5-phenyl-4-hydroxyphenyl group, 3-(4-methylphenyl)-4-hydroxyphenyl group, 5-phenyl-2-hydroxyphenyl group, 5-cumyl-2-hydroxyphenyl group, 3-(1-phenylethyl)-4-hydroxyphenyl group, 3-benzyl-4-hydroxyphenyl group and 3-(4-methylphenyl) methyl-4-hydroxyphenyl group, among others.

The aforementioned corresponding material phenol is a phenol with a substitution number (b) of up to 4, where, if b=4, one whose o-position of the hydroxyl group is not substituted is preferred. A preferred phenol is one whose p-position is not substituted and whose substitution group number (b) 3, where a phenol corresponding to General Formula (4) is particularly preferable.

Also, examples of the aforementioned substitution phenyl group expressed by General Formula (3) or General Formula (4) above include, as those having two or three hydroxyl groups (a is 2 or 3): 2,4-dihydroxyphenyl group, 3,4-dihydroxyphenyl group, 2,5-dihydroxyphenyl group, 2-methyl-4,5-dihydroxyphenyl group, 3-methyl-4,5-dihydroxyphenyl group, 5-methyl-2,4-dihydroxyphenyl group and 2,3,4-trihydroxyphenyl group, among others.

Accordingly, specific examples of the polynuclear polyphenol expressed by General Formula (2) include:
2,2-bis[4,4-bis{3-bis(2,5-dimethyl-4-hydroxyphenyl) methyl-4-methoxycarbonylmethoxy-5-methylphenyl}cyclohexyl]propane,

[Chemical 25]

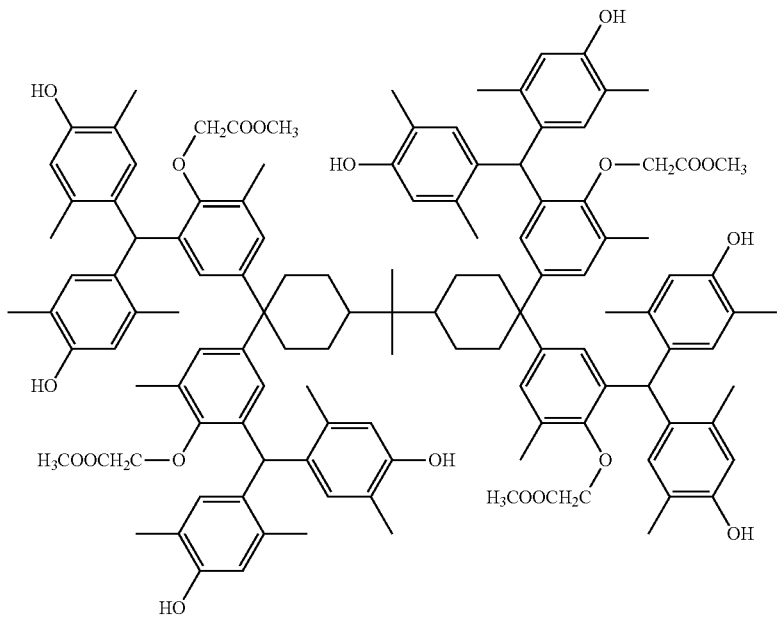

1,1,4,4-tetrakis {3-bis(2,5-dimethyl-4-hydroxyphenyl)methyl-4-methoxycarbonylmethoxy-5-methylphenyl}cyclohexane,
4,4,4',4'-tetrakis{3-bis(2,5-dimethyl-4-hydroxyphenyl)methyl-4-methoxycarbonylmethoxy-5-methylphenyl}-1,1'-bicyclohexane,
bis[4,4-bis {3-bis(2,5-dimethyl-4-hydroxyphenyl)methyl-4-methoxycarbonylmethoxy-5-methylphenyl}cyclohexyl]methane,
2,2-bis[4,4-bis {3-bis(2,5-dimethyl-4-hydroxyphenyl)methyl-4-(4-methoxycarbonylphenyl)methoxy-5-methylphenyl}cyclohexyl]propane,
2,2-bis[4,4-bis{3-bis(4,5-dihydroxy-2-methylphenyl)methyl-4-methoxycarbonylmethoxy-5-methylphenyl}cyclohexyl]propane,
2,2-bis[4,4-bis {3-bis(2,5-dimethyl-4-hydroxyphenyl)methyl-4-carboxymethoxy-5-methylphenyl}cyclohexyl]propane,

[Chemical 26]

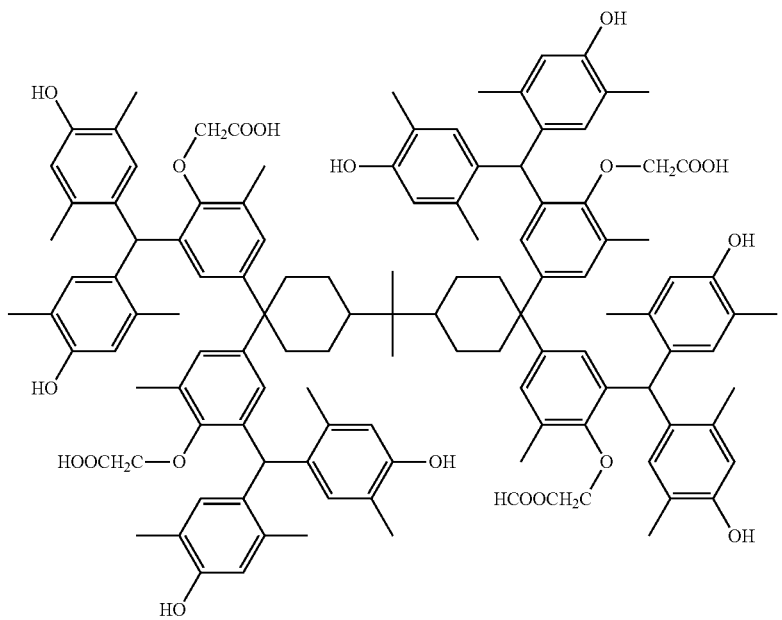

1,1,4,4-tetrakis{3-bis(2,5-dimethyl-4-hydroxyphenyl)methyl-4-carboxymethoxy-5-methylphenyl}cyclohexane, 4,4,4',4'-tetrakis {3-bis(2,5-dimethyl-4-hydroxyphenyl)methyl-4-carboxymethoxy-5-methylphenyl}-1,1'-bicyclohexane, bis[4,4-bis{3-bis(2,5-dimethyl-4-hydroxyphenyl)methyl-4-carboxymethoxy-5-methylphenyl}cyclohexyl]methane, 2,2-bis[4,4-bis{3-bis(2,5-dimethyl-4-hydroxyphenyl)methyl-4-(4-carboxyphenyl)methoxy-5-methylphenyl}cyclohexyl]propane, 2,2-bis[4,4-bis{3-bis(4-hydroxy-3-methylphenyl)methyl-4-carboxymethoxy-5-methylphenyl}cyclohexyl]propane, 2,2-bis[4,4-bis{3-bis(5-cyclohexyl-4-hydroxy-2-methylphenyl)methyl-4-carboxymethoxy-5-methylphenyl}cyclohexyl]propane, 2,2-bis[4,4-bis{3-bis(4-hydroxy-3-isopropyl phenyl)methyl-4-carboxymethoxy-5-methylphenyl}cyclohexyl]propane, and 2,2-bis[4,4-bis {3-bis(2,3,5-trimethyl-4-hydroxyphenyl)methyl-4-carboxymethoxy-5-methylphenyl}cyclohexyl]propane, among others.

The manufacturing method of the second new compound proposed by the present invention, or specifically a polynuclear polyphenol derived from the tetrakis(ether-substituted formylphenyl), as expressed by General Formula (2) above, is not limited in any way, but this compound can be manufactured by, for example, a method similar to the one described in WO2007/142353. For instance, 2,2-bis{4,4-bis(3-formyl-4-methoxycarbonylmethoxy-5-methylphenyl)cyclohexyl}propane and 2,5-dimethylphenol are reacted together to obtain 2,2-bis[4,4-bis {3-bis(2,5-dimethyl-4-hydroxyphenyl)methyl-4-methoxycarbonylmethoxy-5-methylphenyl}cyclohexyl]propane, in which case, as illustrated by Reaction Formula (4) below, a tetrakis(ether-substituted formylphenyl) of the present invention expressed by General Formula (1), which corresponds to the target polynuclear polyphenol compound of the present invention expressed by General Formula (2), is used as the direct material and reacted with a phenol corresponding to the target in the presence of an acid catalyst, to obtain the target polynuclear polyphenol compound.

Reaction Formula (4)

[Chemical 27]

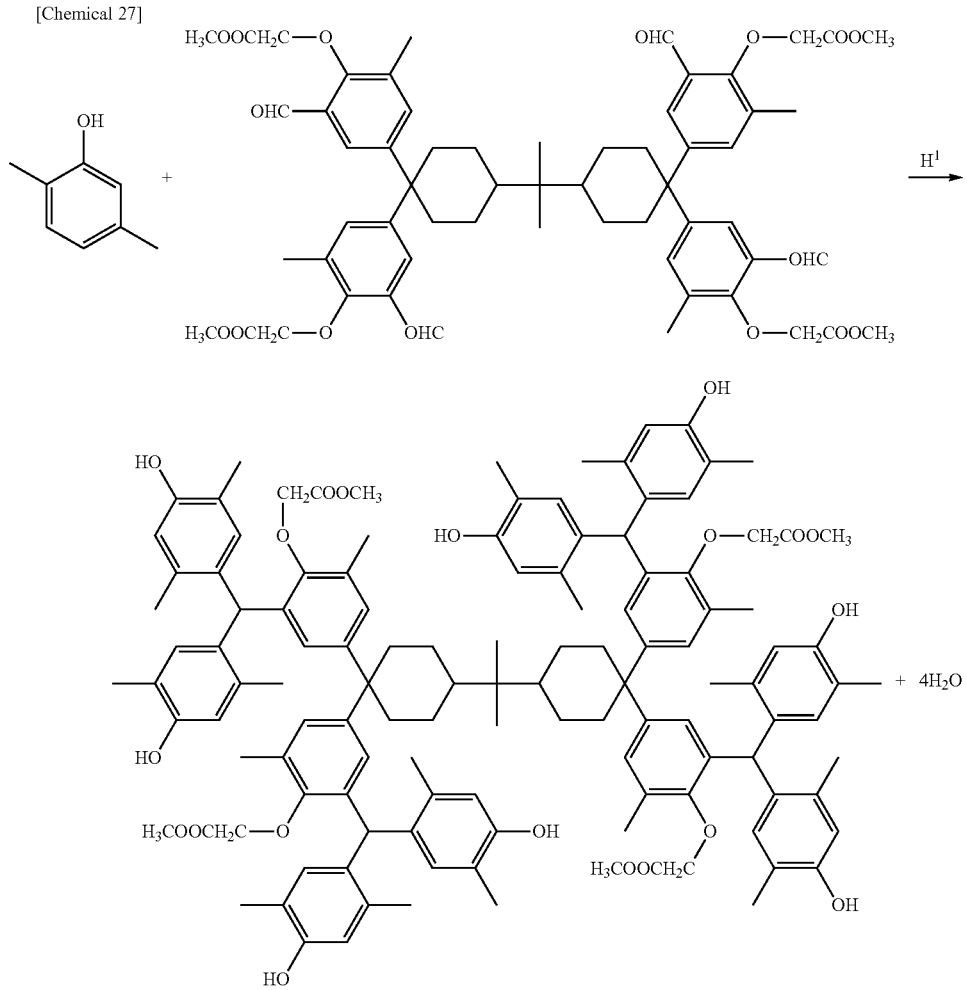

Also, to obtain a polynuclear polyphenol where the ether substitution group has a hydroxycarbonyl hydrocarbon ether substitution group, a method similar to the aforementioned method of obtaining a tetrakis(hydroxycarbonyl hydrocarbon ether-substituted formylphenyl) compound as illustrated by Reaction Formula (3) above can be used, or specifically such polynuclear polyphenol can be obtained with a good yield by hydrolyzing, among corresponding polynuclear polyphenols, an alkoxycarbonyl hydrocarbon group (—R$_2$COOR$_3$) substitution product where R$_3$ is a primary alkyl group, as illustrated by Reaction Formula (5) below.

o-position of the hydroxyl group is not substituted is preferred in terms of synthesis if the substitution group number is 4.

As illustrated by Reaction Formula (4) above, in the reaction of tetrakis(ether-substituted formylphenyl) and phenol the amount of phenol used is normally in a range of 8 to Reaction Formula (5)

[Chemical 28]

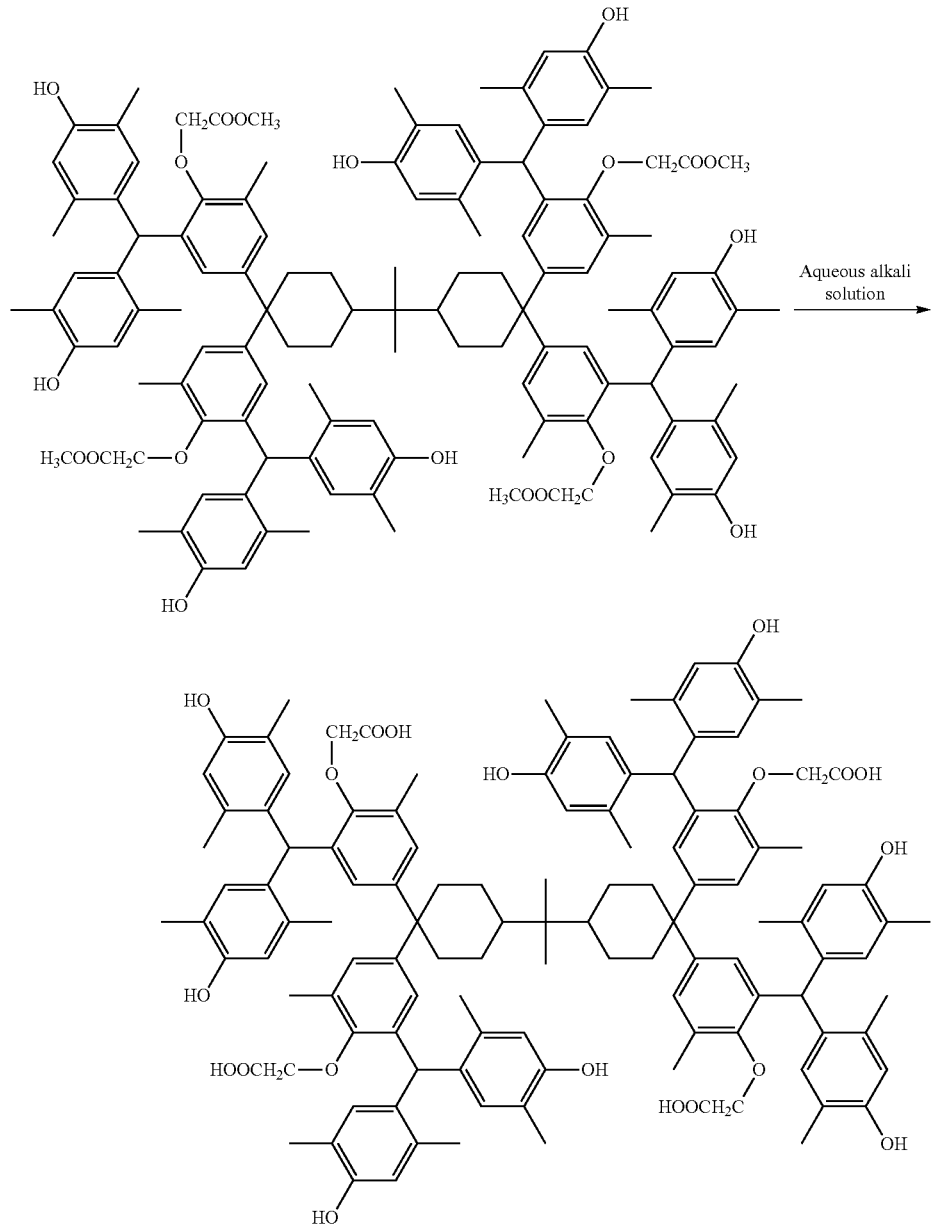

The phenol used above must have at least one of the o-position and p-position of the phenyl nuclear not substituted relative to the hydroxyl group substituting the phenyl nuclear, wherein, to be specific, a phenol whose p-position or m-position relative to the hydroxyl group is not substituted is preferred in terms of synthesis if the substitution group number of the alkyl group, alkoxyl group, aromatic hydrocarbon group, etc., is 3 or less, or a phenol whose 40 mol, or preferably in a range of 9 to 20 mol, per 1 mol of tetrakis(ether-substituted formylphenyl), although the specific range of preferred use amounts varies depending on the phenol used.

Also note that a reaction solvent may or may not be used. However, use of a solvent is preferable if the mol ratio of phenol to tetrakis(ether-substituted formylphenyl) is low or the phenol has a high melting point and thus the mixture cannot be agitated easily. Examples of such a reaction solvent include methanol, butanol and other lower aliphatic alcohols, toluene, xylene and other aromatic hydrocarbons, methylisobutylketone and other aliphatic ketones, and other solvents constituted by a mixture thereof. Among others, lower aliphatic alcohols are preferred, and when catechol, resorcin or other type of phenol having a high melting point and high solubility in water is used, water can be used as the reaction solvent.

Such a solvent is used normally in a range of 0.5 part by weight to 10 parts by weight, or preferably in a range of 0.5 part by weight to 2 parts by weight, relative to the phenol used, although the amount used is not specifically limited.

Under the manufacturing method illustrated by Reaction Formula (4) above, the acid catalyst is preferably an acid that dissolves in the reaction mixture, and therefore an inorganic acid, or organic sulfonic acid, carboxylic acid or other organic acid, of strong to medium acidity is used. Specific examples include 35% hydrochloric acid, hydrogen chloride gas, sulfuric acid, phosphoric acid and other inorganic acids, as well as p-toluene sulfonic acid, methane sulfonic acid, oxalic acid and other organic acids. Such an acid catalyst is used normally in a range of 1 percent by weight to 50 percent by weight relative to the phenol, although a preferred range of use amounts varies depending on the acidity, etc.

The reaction can be implemented at temperatures normally in a range of 0° C. to 100° C., or preferably in a range of 20° C. to 60° C., in air, or more preferably in an atmosphere of nitrogen or other inert gas, normally for 2 to 20 hours or so under agitation.

Under the aforementioned manufacturing method, the polynuclear phenol compound produced by the reaction can be separated and refined, as necessary, according to any known method.

After the reaction is complete, therefore, aqueous sodium hydroxide solution or other alkali water is added to the obtained reaction liquid to neutralize the acid, after which toluene, xylene, methylisobutylketone, ether or other solvent that can be separated from water is added, as necessary, to separate and remove the water layer, and the water layer is separated while the oil layer is washed in water at the same time and then the solvent and non-reacting material phenol are removed by distillation from the obtained oil layer, as necessary, after which a solvent is added to cause crystallization or precipitation to filter out crystalline or non-crystalline solids. If necessary, a similar crystallization or precipitation operation may be repeated once or several times to isolate solids of higher purity.

If isolating the target polynuclear phenol compound from the reaction product is difficult by the aforementioned means of crystallization or precipitation, column separation may be used to obtain and refine the target compound, or the solvent may be distilled or otherwise removed from the oil layer in which the compound is dissolved in the aforementioned refinement process to obtain the target compound.

With respect to the polynuclear polyphenol compound expressed by General Formula (2), the manufacturing method to obtain a hydroxycarbonyl hydrocarbon ether substitution product of the ether group when $R_3$ is a hydrogen atom is not limited in any way. However, such a hydroxycarbonyl hydrocarbon ether substitution group ($-O-R_2COOH$) can be obtained easily by, for example, using sodium hydroxide, tetramethylammonium hydroxide or other aqueous alkali solution to ester hydrolyze an alkoxyl carbonyl hydrocarbon ether-substituted polynuclear polyphenol compound where $R_3$ is a primary alkyl group according to General Formula (2) based on a method similar to the one for obtaining a tetrakis(hydroxycarboxy hydrocarbon ether-substituted formylphenyl) according to Reaction Formula (3) above.

Also, the obtained reaction product can be refined according to any know method and can be refined to higher purity, if necessary.

Next, the third new compound proposed by the present invention, or specifically a new polynuclear polyphenol containing an acid-cleavable group, is expressed by General Formula (5) below.

[Chemical 29]

General Formula (5)

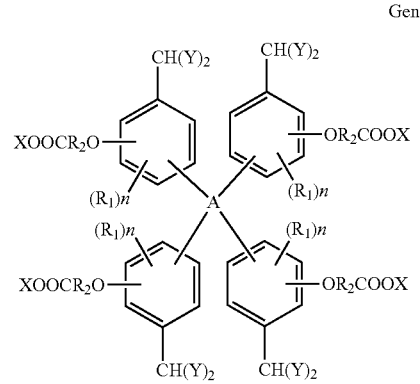

(In the formula, $R_1$, n, $R_2$ and A are the same as the corresponding items in General Formula (1) above, while the four X's are each a hydrogen atom or acid-cleavable group expressed by General Formula (6) below, but in the formula, all four X's are not a hydrogen atom at the same time, and Y is the same as the corresponding item in General Formula (2) above)

[Chemical 30]

General Formula (6)

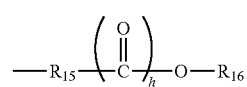

(In the formula, $R_{15}$ represents an alkylene group with 1 to 8 carbon atoms, $R_{16}$ represents a saturated hydrocarbon group with 1 to 30 carbon atoms, and h represents 0 or 1, where, if h is 1, $R_{16}$ represents a tertiary saturated hydrocarbon group with 4 to 30 carbon atoms.)

Under the present invention, in General Formula (5), it is preferable that at least one, or more preferably three or more, or most preferably all, of the four X's in the molecule be an acid-cleavable group expressed by General Formula (6) above.

In a polynuclear polyphenol conforming to the present invention, the acid-cleavable group bonding with the phenyl group inside the molecule is a group where the X group itself cleaves due to the action of acid or $R_{16}$ cleaves to produce carboxylic acid. Normally if h=1, $R_{16}$ cleaves, and if h=0, the X group itself cleaves.

In the formula, $R_{15}$ represents an alkylene group with 1 to 8 carbon atoms, $R_{16}$ represents a saturated hydrocarbon group with 1 to 30 carbon atoms, and h represents 0 or 1. If h is 1, $R_{16}$ represents a tertiary saturated hydrocarbon group with 4 to 30 carbon atoms.

The alkylene group with 1 to 8 carbon atoms as represented by $R_{15}$ has preferably 1 to 4 carbon atoms, or specifically it is a straight-chain or branched-chain alkylene group with 1 to 8 carbon atoms. If h=0, a preferred form of $R_{15}$ is expressed by General Formula (6r) below.

[Chemical 31]

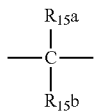

General Formula (6r)

(In the formula, $R_{15}a$ and $R_{15}b$ respectively represent independently a hydrogen atom or alkyl group with 1 to 7 carbon atoms, but the total number of carbon atoms of $R_{15}a+R_{15}b$ is 7 or less.)

Therefore, specific examples of $R_{15}$ include methylene, ethylene, ethane-1,1-diyl, propylene, propane-1,1-diyl, butylene, ethylethylene, 2-methyl-1,3-propylene, 2-methyl butane-1,4-diyl, pentamethylene, hexamethylene, 1,1,2,2-tetramethylethylene, isopropylmethylene and 1,1-diethylmethylene, among others. Also, h is 0 or 1.

If h is 0, $R_{16}$ represents a monovalent saturated hydrocarbon group with 1 to 30 carbon atoms, or preferably 1 to 20, where specific examples include straight-chain, branched-chain saturated hydrocarbon groups as well as monocyclic, fused-ring, bridged-ring, and other polycyclic saturated hydrocarbon groups, among others. Any such cyclic saturated hydrocarbon group may have the methyl or ethyl group or other lower saturated hydrocarbon group or other substitution group in the ring. Accordingly, specific examples of the aforementioned straight-chain and branched-chain saturated hydrocarbon groups include the methyl group, ethyl group, n-propyl group, n-butyl group, isobutyl group, n-pentyl group, isobutyl group, t-butyl group, isopentyl group, neopentyl group and other chained saturated hydrocarbon groups. Examples of cyclic saturated hydrocarbon groups include cyclopentyl, cyclohexyl and other cyclic secondary saturated hydrocarbon groups, adamantyl, norbornane-2-yl, isobornane-2-yl, tricyclodecane-2-yl and other polycyclic saturated hydrocarbon groups. Among others, cyclic saturated hydrocarbon groups where the carbon atom of $R_{16}$ bonding with the oxy group is primary or secondary according to General Formula (6) are preferable, where a preferable number of carbon atoms is 7 to 15. In particular, the adamantyl group and other polycyclic saturated hydrocarbon groups are preferred.

If h is 1, $R_{16}$ represents a tertiary saturated hydrocarbon group with 4 to 30 carbon atoms, where the carbon atom of $R_{16}$ bonding with the oxy group is tertiary according to General Formula (6), as expressed by General Formula (6s) below.

[Chemical 32]

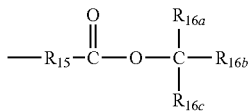

General Formula (6s)

(In the formula, $R_{15}$ is the same as the corresponding item in General Formula 6, and $R_{16a}$, $R_{16b}$ and $R_{16c}$ respectively represent independently a saturated hydrocarbon group with 1 to 27 carbon atoms, where $R_{16a}$, $R_{16b}$ and $R_{16c}$ may bond together and form a ring, but the total number of carbon atoms of $R_{16a}+R_{16b}+R_{16c}$ is 29 or less.)

$R_{16}$ has preferably 4 to 20 carbon atoms, where specific examples include branched tertiary saturated hydrocarbon groups, tertiary cyclic saturated hydrocarbon groups and tertiary polycyclic saturated hydrocarbon groups. Any such cyclic saturated hydrocarbon group may have the methyl or ethyl group or other lower saturated hydrocarbon group or other substitution group in the ring. Specific examples of the aforementioned branched tertiary saturated hydrocarbon groups include t-butyl, t-amyl and t-octyl, among others. The aforementioned tertiary cyclic saturated hydrocarbon groups are monocyclic, fused-ring, bridged-ring and other polycyclic saturated hydrocarbon groups, such as 1-methyl-1-cyclohexyl (Chemical 33), 1-methyl-1-cyclopentyl, 2-methylbicyclo[2.2.1]hepto-2-yl(Chemical 33), 2-methyl-2-adamantyl (Chemical 33), 1-adamantyl and 3-methyltetracyclo[4.4.0.1$^{2,5}$.1$^{7,10}$]dodeca-3-yl (Chemical 33), among others. Of these, tertiary cyclic saturated hydrocarbon groups and tertiary polycyclic saturated hydrocarbon groups are preferred, where the number of carbon atoms is preferably 8 to 15. In particular, the tertiary adamantyl group and other tertiary polycyclic saturated hydrocarbon groups are preferred.

[Chemical 33]

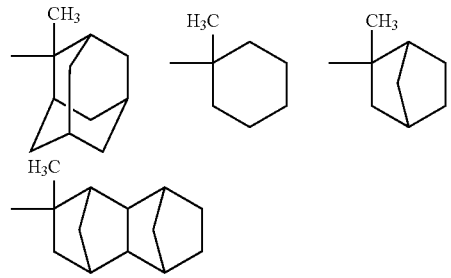

Accordingly, specific examples of a preferred form of the acid-cleavable group expressed by General Formula (6) above include acid-cleavable groups expressed by General Formulas (6a) to (6e) below.

[Chemical 34]

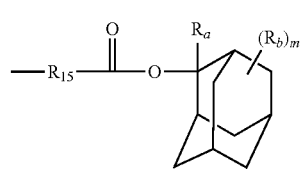

General Formula (6a)

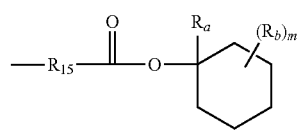

General Formula (6b)

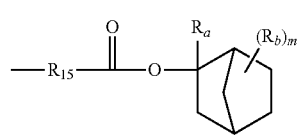

General Formula (6c)

-continued

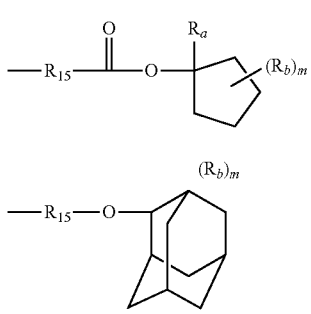

General Formula (6d)

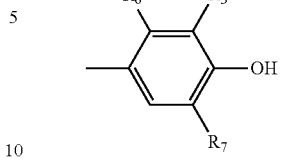

General Formula (4)

General Formula (6e)

In General Formulas (6a) to (6e) above, Ra and Rb in each formula represent a straight-chain or branched-chain alkyl group, or preferably an alkyl group with 1 to 4 carbon atoms. Also, m represents 0 or an integer of 1 to 4. $R_{15}$ is the same as the corresponding item in General Formula (6).

In General Formula (5), it is preferable that at least one, or more preferably three or more, or most preferably all, of the four X's in the molecule be an acid-cleavable group expressed by General Formula (6) above.

In addition, the ether-substituted phenyl group in General Formula (5) is preferably one expressed by General Formula (12) below.

[Chemical 35]

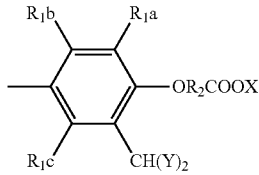

General Formula (12)

In the formula, $R_1a$, $R_1b$ and $R_1c$ are the same as $R_1$ in General Formula (1), while X and Y are the same as the corresponding items in General Formula (5). In General Formula (12), $R_1a$ is preferably an alkyl group, while $R_1b$ and $R_1c$ are preferably both a hydrogen atom.

Also in General Formula (5), in the formula, Y is a hydroxyl phenyl group expressed by General Formula (3).

[Chemical 36]

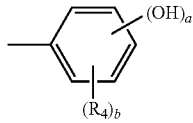

General Formula (3)

In the formula, $R_4$ represents an alkyl group with 1 to 8 carbon atoms or alkoxyl group with 1 to 8 carbon atoms, or aromatic hydrocarbon group or saturated hydrocarbon group with 1 to 8 carbon atoms having an aromatic hydrocarbon group, a represents an integer of 1 to 3, and b represents 0 or an integer of 1 to 4, where 1≤a+b≤5 and if b is 2 or greater, $R_4$ may be the same or different.

In addition, the hydroxyphenyl group expressed by General Formula (3) above is preferably one expressed by General Formula (4) below.

[Chemical 37]

In the formula, $R_5$, $R_6$ and $R_7$ respectively represent independently a hydrogen atom or alkyl group with 1 to 8 carbon atoms or alkoxyl group with 1 to 8 carbon atoms or aromatic hydrocarbon group or saturated hydrocarbon group with 1 to 8 carbon atoms having an aromatic hydrocarbon group. For the alkyl group, alkoxyl group or aromatic hydrocarbon group or saturated hydrocarbon group with 1 to 8 carbon atoms having an aromatic hydrocarbon group as represented by $R_4$ or any one of $R_5$ to $R_7$, specifically it is the same as the alkyl group, alkoxyl group or aromatic hydrocarbon group or saturated hydrocarbon group with 1 to 8 carbon atoms having an aromatic hydrocarbon group as represented by $R_1$. The alkyl group is preferably a straight-chain or branched-chain alkyl group with 1 to 4 carbon atoms or cycloalkyl group with 5 to 7 carbon atoms, while the alkoxyl group is preferably an alkoxyl group with 1 to 4 carbon atoms or cycloalkoxyl group with 5 to 7 carbon atoms, while the aromatic hydrocarbon is preferably a phenyl group.

If b=4, or $R_4$ is substituted in four positions in General Formula (3), a substitution group that can bond with the formyl group in the o-position relative to the hydroxyl group is preferred in terms of synthesis.

To be specific, therefore, examples of the substitution phenyl group expressed by General Formula (3) or General Formula (4) above include, as those having one hydroxyl group: 4-hydroxyphenyl group, 3-methyl-4-hydroxyphenyl group, 2-methyl-4-hydroxyphenyl group, 3,6-dimethyl-4-hydroxyphenyl group, 2,5-dimethyl-4-hydroxyphenyl group, 3,5-dimethyl-4-hydroxyphenyl group, 2,3,5-trimethyl-4-hydroxyphenyl group, 3-ethyl-4-hydroxyphenyl group, 3-isopropyl-4-hydroxyphenyl group, 3-t-butyl-4-hydroxyphenyl group, 3-t-butyl-6-methyl-4-hydroxyphenyl group, 3,5-di-t-butyl-4-hydroxyphenyl group, 3-sec-butyl-4-hydroxyphenyl group, 3-t-octyl-4-hydroxyphenyl group, 3-t-butyl-5-methyl-4-hydroxyphenyl group, 2-cyclohexyl-4-hydroxyphenyl group, 3-cyclohexyl-4-hydroxyphenyl group, 2-cyclohexyl-5-methyl-4-hydroxyphenyl group, 2-methyl-5-cyclohexyl-4-hydroxyphenyl group, 5-methyl-2-hydroxyphenyl group, 4,6-dimethyl-2-hydroxyphenyl group, 3,4,6-trimethyl-2-hydroxyphenyl group, 3,5-di-t-butyl-2-hydroxyphenyl group, 5-t-octyl-2-hydroxyphenyl group, 3-methoxy-4-hydroxyphenyl group, 5-methoxy-4-hydroxyphenyl group, 3-n-hexyl oxy-4-hydroxyphenyl group, 3-n-octyloxy-4-hydroxyphenyl group, 5-butoxy-2-hydroxyphenyl group, 3-phenyl-4-hydroxyphenyl group, 3-methyl-5-phenyl-4-hydroxyphenyl group, 3-(4-methylphenyl)-4-hydroxyphenyl group, 5-phenyl-2-hydroxyphenyl group, 5-cumyl-2-hydroxyphenyl group, 3-(1-phenylethyl)-4-hydroxyphenyl group, 3-benzyl-4-hydroxyphenyl group and 3-(4-methylphenyl) methyl-4-hydroxyphenyl group, among others.

Preferred among the above are phenols whose substitution number (b) is up to 4 (if b=4, those whose o-position of the hydroxyl group is not substituted are preferred) as well as phenols whose p-position or m-position is not substituted and whose substitution group number (b)≤3, of which phenols corresponding to General Formula (4) are particularly preferable.

Also, examples of the phenyl group include, as those having two or three hydroxyl groups: 2,4-dihydroxyphenyl group, 3,4-dihydroxyphenyl group, 2,5-dihydroxyphenyl group, 2-methyl-4,5-dihydroxyphenyl group, 3-methyl-4,5-dihydroxyphenyl group, 5-methyl-2,4-dihydroxyphenyl group and 2,3,4-trihydroxyphenyl group, among others.

In General Formula (5), A is the bonding group of the ether-substituted phenyl group and also the center skeleton is a tetravalent carbon atom group or tetravalent saturated hydrocarbon group with 2 or more carbon atoms, or preferably a tetravalent saturated hydrocarbon group with 2 to 30 carbon atoms. The tetravalent saturated hydrocarbon group may be a straight-chain or branched-chain saturated hydrocarbon group, monocyclic, fused-ring, bridged-ring, polycyclic or other cyclic saturated hydrocarbon group, all of which may have a substitution group, or a saturated hydrocarbon group containing both a chained variation and cyclic variation thereof, etc. Of these, those expressed below are preferred forms of the aforementioned saturated hydrocarbon group, for example.

[Chemical 38]

Formula

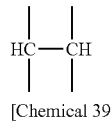

Formula

[Chemical 39]

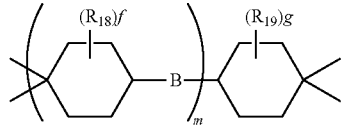

General Formula (13)

(In the formula, $R_{18}$ and $R_{19}$ respectively represent independently an alkyl group with 1 to 8 carbon atoms, f and g respectively represent independently 0 or an integer of 1 to 4, B represents a single bond or divalent saturated hydrocarbon group with 1 to 10 carbon atoms, and m represents 0 or 1. The divalent saturated hydrocarbon group is a straight-chain, branched-chain or cyclic alkylene group with 1 to 10 carbon atoms.)

In General Formula (13) above, the alkyl group with 1 to 8 carbon atoms as represented by $R_{18}$ or $R_{19}$ may be, for example, methyl, n-propyl, n-butyl or other straight-chain saturated hydrocarbon group, t-butyl, isobutyl or other branched-chain saturated hydrocarbon group, or cyclohexyl, cyclopentyl or other cyclic saturated hydrocarbon group. On the other hand, specific examples of the divalent saturated hydrocarbon group with 1 to 10 carbon atoms as represented by B include methylene, ethylene, ethane-1,1-diyl, propylene, propan-1,1-diyl, butylene, ethylethylene, 2-methyl-1,3-propylene, 2-methylbutane-1,4-diyl, pentamethylene, hexamethylene, 1,1,2,2-tetramethylethylene, isopropylmethylene, 1,1-diethylmethylene and other alkylene groups.

Also, f and g are preferably 0 or 1, and if for g is 1, and m is 1, the substitution position of $R_{18}$ or $R_{19}$ is preferably position 2 relative to the bonding location with the B group. If for g is 2 or greater, it is preferable that each alkyl group bond with a different carbon.

Accordingly, preferred forms of the tetravalent saturated hydrocarbon group expressed by General Formula (13) above include those shown below.

[Chemical 40]

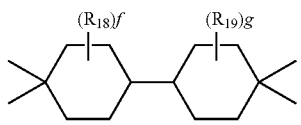

[Chemical 41]

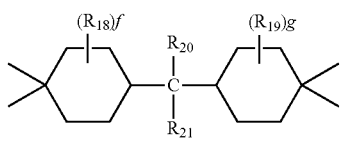

General Formula (14)

(In the formula, $R_{18}$, $R_{19}$, f and g are the same as the corresponding items in General Formula (13), while $R_{20}$ and $R_{21}$ respectively represent independently a hydrogen atom or alkyl group with 1 to 9 carbon atoms. However, the total number of carbon atoms of $R_{20}+R_{21}$ is 9 or less. The alkyl group with 1 to 9 carbon atoms is a straight-chain alkyl group with 1 to 9 carbon atoms or branched-chain or cyclic alkyl group with 3 to 10 carbon atoms.)

As for the saturated hydrocarbon group expressed by General Formula (14), the following tetravalent saturated hydrocarbon groups are preferred, among others.

[Chemical 42]

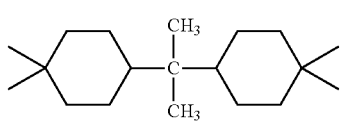

Formula

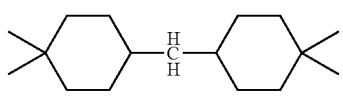

Formula

Accordingly, specific examples of the polynuclear polyphenol expressed by General Formula (5) above include:

2,2-bis{4,4-bis[3-bis(2,5-dimethyl-4-hydroxyphenyl) methyl-4-(2-methyl-2-adamantyl)oxycarbonylmethoxycarbonylmethoxy-5-methylphenyl]cyclohexyl}propane (Compound 1),

[Chemical 43]
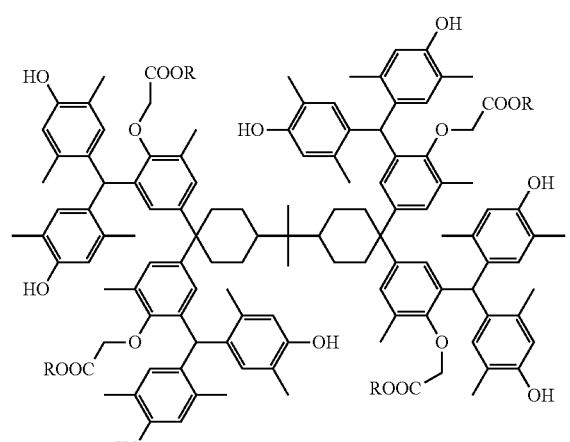
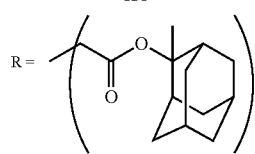
4,4,4',4'-tetrakis[3-bis(2,5-dimethyl-4-hydroxyphenyl) methyl-4-(2-methyl-2-adamantyl)oxycarbonyl methoxycarbonylmethoxy-5-methylphenyl]-1,1'-bicyclohexane (Compound 2), and
[Chemical 44]
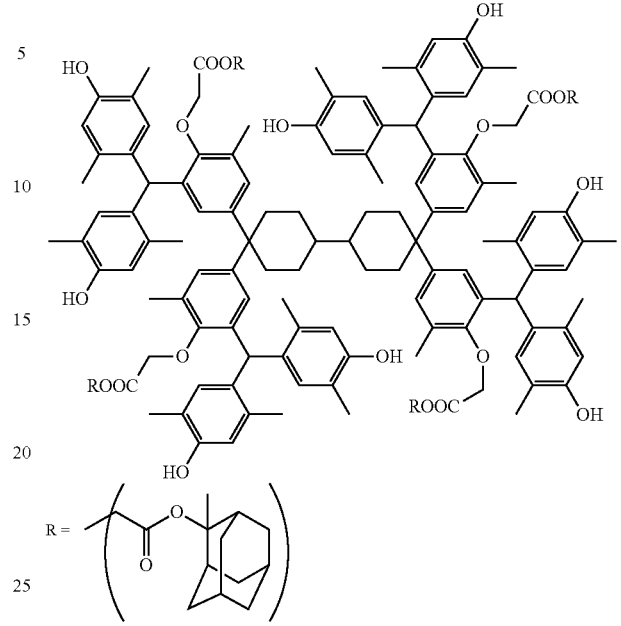
1,1,4,4-tetrakis[3-bis(2,5-dimethyl-4-hydroxyphenyl) methyl-4-(2-methyl-2-adamantyl)oxycarbonyl methoxycarbonylmethoxy-5-methylphenyl]cyclohexane (Compound 3).
[Chemical 45]
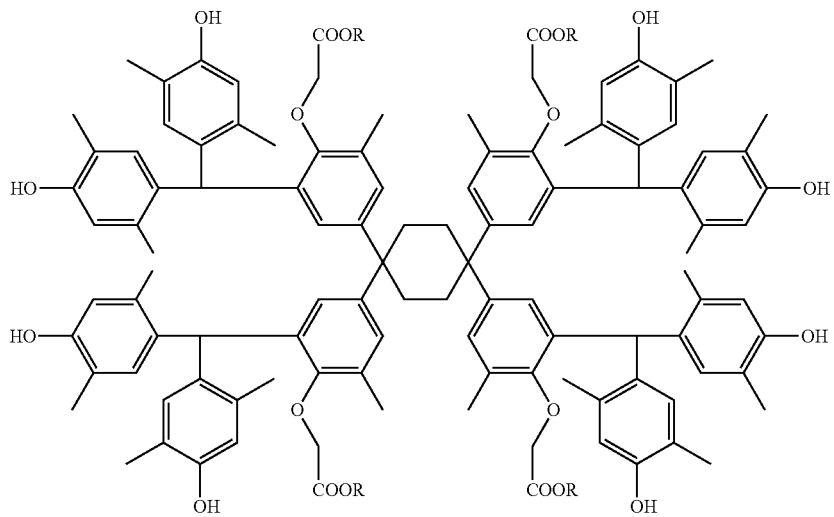
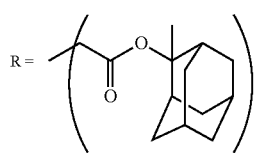

2,2-bis[4,4-bis {3-bis(2,5-dimethyl-4-hydroxyphenyl) methyl-4-[4-(2-ethyl-2-adamantyl)oxycarbonylmethoxycarbonylphenyl]methoxy-5-methylphenyl}cyclohexyl] propane, 2,2-bis{4,4-bis[3-bis(2-methyl-4,5-dihydroxyphenyl) methyl-4-(2-methyl-2-adamantyl)oxycarbonylmethoxycarbonylmethoxy-5-methylphenyl]cyclohexyl}propane, 2,2-bis {4,4-bis[3-bis(2,5-dimethyl-4-hydroxyphenyl) methyl-4-(1-methyl-1-cyclohexyl)oxycarbonylmethoxycarbonylmethoxy-5-methylphenyl]cyclohexyl}propane, 2,2-bis{4,4-bis[3-bis(2,5-dimethyl-4-hydroxyphenyl) methyl-4-(1-methyl-1-cyclopentyl)oxycarbonylmethoxycarbonylmethoxy-5-methylphenyl]cyclohexyl}propane, and 2,2-bis {4,4-bis[3-bis(2,5-dimethyl-4-hydroxyphenyl) methyl-4-(2-adamantyl)oxy methoxycarbonylmethoxy-5-methylphenyl]cyclohexyl}propane, among others.

The manufacturing method of such polynuclear polyphenol conforming to the present invention, as expressed by General Formula (5) above, is not limited in any way and it can be obtained, for example, by using as the direct material a hydroxycarbonyl hydrocarbon ether-substituted polynuclear polyphenol compound expressed by General Formula (15) below and corresponding to the target polynuclear polyphenol compound expressed by General Formula (5), and causing it to react with a halogenated alkoxy or alkoxycarbonyl hydrocarbon expressed by General Formula (16) below in a solvent in the presence of a base, as illustrated by Reaction Formula (6) below.

Reaction Formula (6)

[Chemical 46]

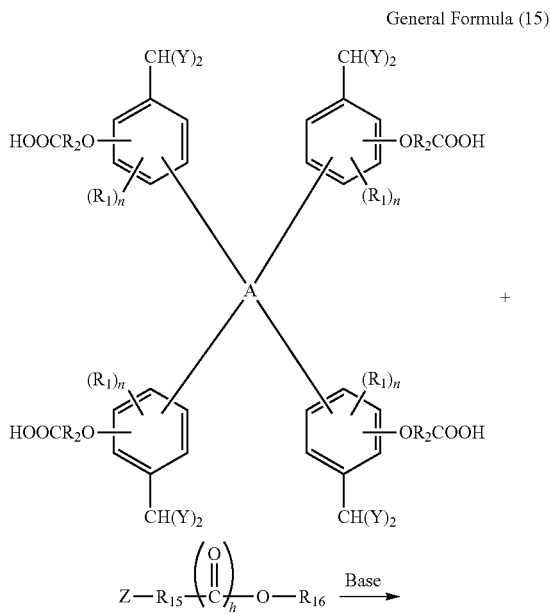

General Formula (15)

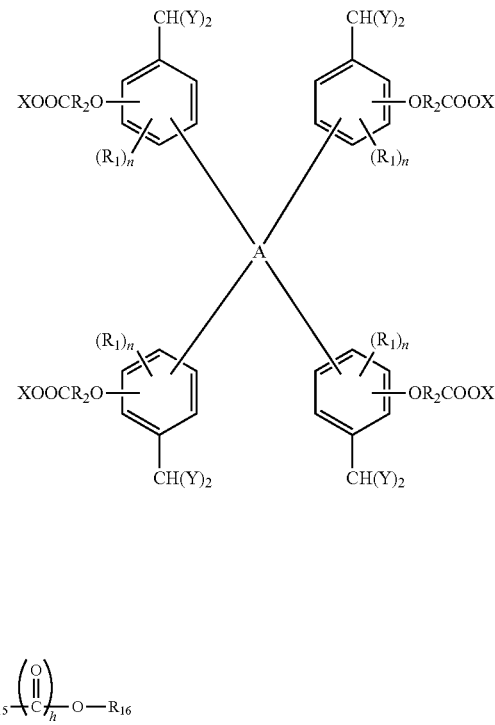

General Formula (16)

In General Formula (15), in the formula, $R_1$, n, $R_2$, A and Y are the same as the corresponding items in General Formula (5) above. In General Formula (16), in the formula, $R_{15}$, $R_{16}$ and h are the same as the corresponding items in General Formula (6) above, while Z represents a halogen atom.

Also, the hydroxycarbonyl hydrocarbon ether-substituted polynuclear polyphenol compound expressed by General Formula (15) can be obtained, as illustrated by Reaction Formula (5), by hydrolyzing an alkoxyl carbonyl hydrocarbon ether-substituted polynuclear polyphenol compound whose $R_3$ is a primary alkyl group according to General Formula (2) above.

A specific example is given where the target polynuclear polyphenol is 2,2-bis{4,4-bis[3-bis(2,5-dimethyl-4-hydroxyphenyl)methyl-4-(2-methyl-2-adamantyl)oxycarbonylmethoxycarbonylmethoxy-5-methylphenyl] cyclohexyl}propane, in which case, as shown by Reaction Formula (7) below, such target polynuclear polyphenol can be obtained by using as the direct material a carboxyl methoxy-substituted polynuclear polyphenol compound corresponding to the aforementioned target polynuclear polyphenol, or specifically 2,2-bis{4,4-bis[3-bis(2,5-dimethyl-4-hydroxyphenyl)methyl-4-carboxymethoxy-5-methylphenyl]cyclohexyl}propane, and then causing it to react with, for example, 2-methyl-2-adamantyl bromoacetate as a halogenated alkoxy or alkoxycarbonyl hydrocarbon.

Reaction Formula (7)
[Chemical 47]
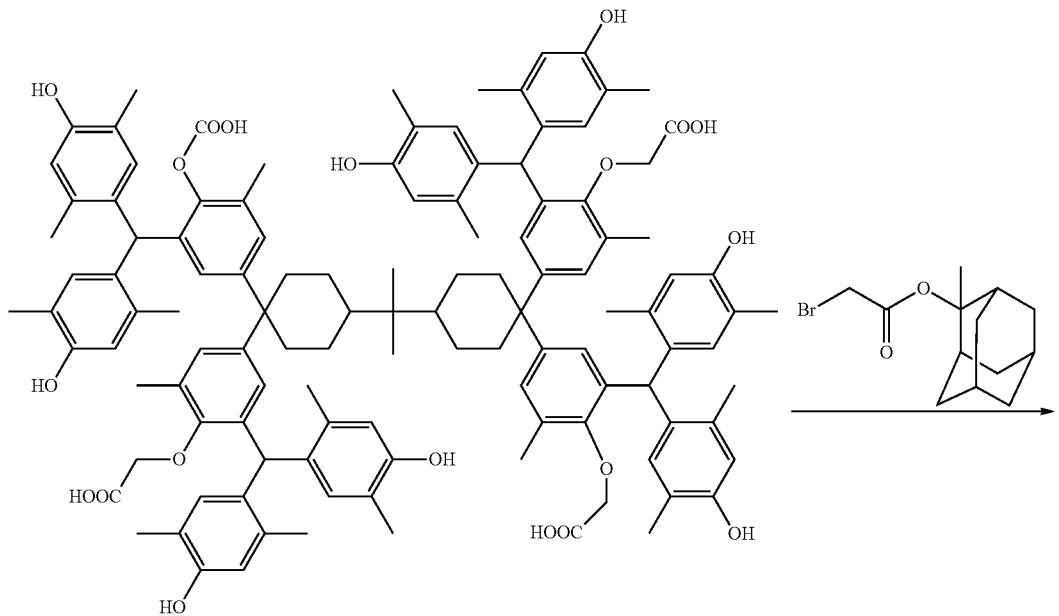
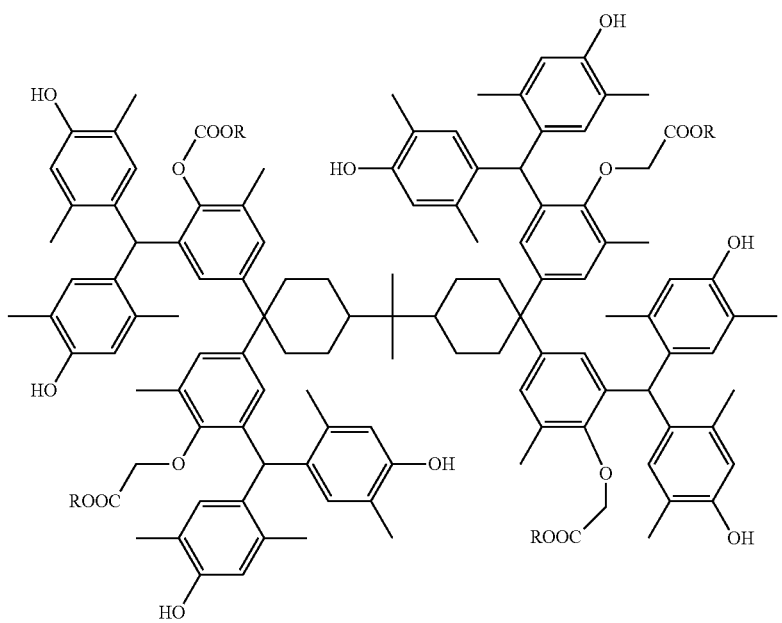
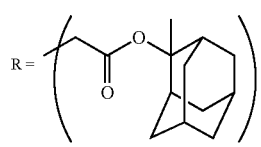

Under the manufacturing method illustrated by Reaction Formula (6) above pertaining to a polynuclear polyphenol expressed by General Formula (5) conforming to the present invention, specific examples of the carboxy hydrocarbon ether-substituted polynuclear polyphenol used as the direct material and expressed by General Formula (15) above include, when cited in correspondence with each polynuclear polyphenol expressed by General Formula (5), 2,2-bis{4,4-bis[3-bis(2,5-dimethyl-4-hydroxyphenyl)methyl-4-carboxymethoxy-5-methylphenyl]cyclohexyl}propane corresponding to Compound 1 above,

[Chemical 48]

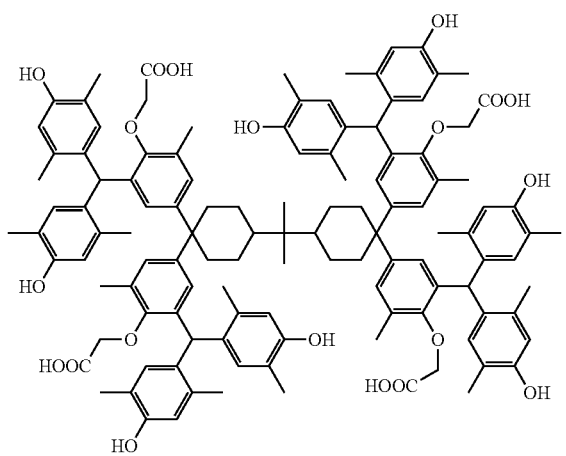

4,4,4',4'-tetrakis[3-bis(2,5-dimethyl-4-hydroxyphenyl)methyl-4-carboxymethoxy-5-methylphenyl]-1,1'-bicyclohexane corresponding to Compound 2 above, and

[Chemical 49]

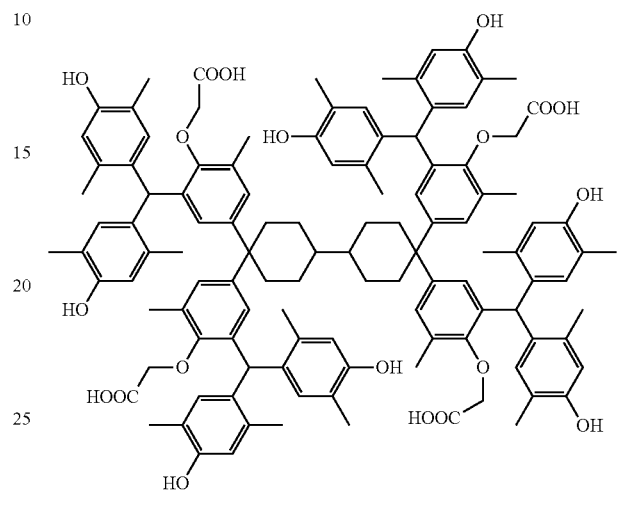

1,1,4,4-tetrakis[3-bis(2,5-dimethyl-4-hydroxyphenyl)methyl-4-carboxymethoxy-5-methylphenyl]cyclohexane corresponding to Compound 3 above.

[Chemical 50]

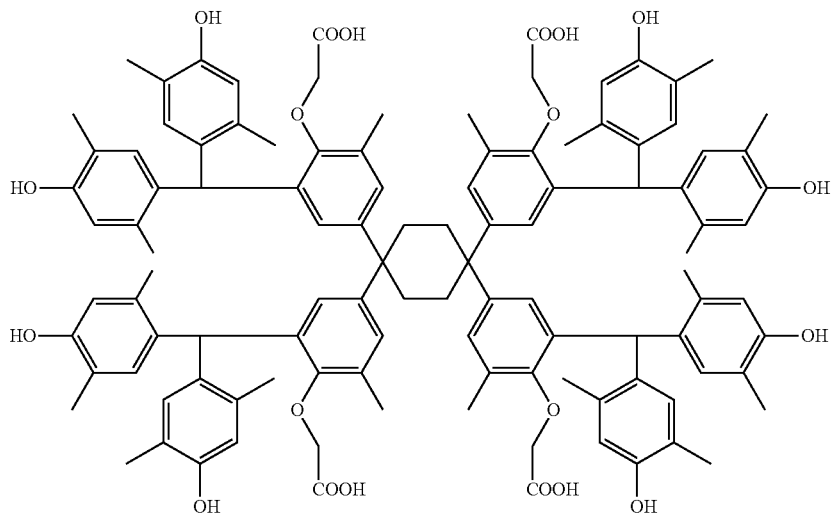

Similarly, other examples include:

2,2-bis {4,4-bis[3-bis(2-methyl-5-cyclohexyl-4-hydroxyphenyl)methyl-4-carboxymethoxy-5-methylphenyl]cylohexyl}propane, 2,2-bis[4,4-bis{3-bis(2,5-dimethyl-4-hydroxyphenyl)methyl-4-(4-carboxyphenyl)methoxy-5-methylphenyl}cyclohexyl]propane, and 2,2-bis{4,4-bis[3-bis(2-methyl-4,5-dihydroxyphenyl)methyl-4-carboxymethoxy-5-methylphenyl]cyclohexyl}propane, among others.

As for the halogenated alkoxy or alkoxycarbonyl hydrocarbon expressed by General Formula (16) above, which is reacted with the direct material or specifically hydroxycarbonyl hydrocarbon ether-substituted polynuclear polyphenol expressed by General Formula (15) above, Z in the formula represents a halogen atom, where the halogen atom is chlorine, bromine or iodine, etc., or preferably bromine or chlorine. Also, $R_{15}$, $R_{16}$ and h are the same as the corresponding items in General Formula (6) above. Accordingly, specific examples of the halogenated alkoxy or alkoxycarbonyl hydrocarbon include 2-methyl-2-adamantylchloroacetate, t-butyl chloroacetate, 2-methyl-2-adamantylbromoacetate, 2-ethyl-2-adamantylbromoacetate, t-butyl bromoacetate, 2-chloromethoxyadamantane and chloromethoxymethyl cyclohexane, among others.

For the base used in the reaction, either an organic base or inorganic base can be used, but the organic base is preferably triethyl amine, tributyl amine or other tertiary amine, for example, while the inorganic base is preferably potassium carbonate, sodium carbonate or other alkali metal carbonate, for example. Of these, an organic salt is preferred, and triethyl amine or other tertiary amine is more preferred.

The amount of base used is normally in a range of 1 to 8 mol per 1 mol of the hydroxycarbonyl ether-substituted polynuclear polyphenol compound expressed by General Formula (15), or in a range of 4 to 8 mol, or preferably in a range of 4 to 5 mol, if all carboxyl groups are to be substituted.

Also, the amount of halogenated alkoxy or alkoxycarbonyl hydrocarbon expressed by General Formula (16) above is normally in a range of 1 to 8 mol per 1 mol of the hydroxycarbonyl hydrocarbon ether-substituted polynuclear polyphenol compound expressed by General Formula (15), or in a range of 4 to 8 mol, or preferably in a range of 4 to 5 mol, if all carboxyl groups are to be substituted.

The solvent used in the reaction is preferably dioxane, THF or other ether, dimethylformamide, dimethylacetoamide or other amide, dimethylsulfoxide, pyridine, 4-methylpyridine, N-methylpyrrolidone or other amine, or any mixture thereof.

The amount of solvent used is normally in a range of 1 part by weight to 10 parts by weight, or preferably in a range of 2 to 5 parts by weight, per 1 part by weight of the direct material or specifically carboxyhydrocarbon ether-substituted polynuclear polyphenol from the viewpoint of reaction volume ratio, etc.

If necessary, potassium iodide or other alkali metal iodide, copper, copper chloride or other copper compound, tetrabutylammonium bromide or other phase transfer catalyst, or any other reaction accelerator additive, can be added to accelerate the etherification reaction.

Although the method and order of introducing the reaction materials are not limited, normally it is preferable to mix together the material carboxy hydrocarbon ether-substituted polynuclear polyphenol and base to produce an oxy salt, and then add to this mixture liquid the halogenated alkoxy or alkoxycarbonyl hydrocarbon expressed by General Formula (16).

The reaction can be implemented at temperatures normally in a range of 0° C. to 100° C., or preferably in a range of 20° C. to 50° C., for several hours, such as 2 to 20 hours. The reaction pressure is normally in a range of slight decompression to slight compression, or preferably around normal pressure.

After the reaction is complete, the target can be obtained from the reaction mixture using any known method. For example, an organic solvent such as toluene or cyclohexane, etc., is added to the reaction mixture as deemed appropriate, along with water, to wash the mixture to remove the water layer, after which water is added to the oil layer, if necessary, followed by agitation and washing to remove the solvent by distillation from the oil layer, to obtain the target polynuclear polyphenol conforming to the present invention as expressed by General Formula (5). If the target polynuclear polyphenol must have higher purity, add methanol or other aliphatic lower alcohol and, if necessary, toluene or other aromatic hydrocarbon or methylethylketone or other aliphatic ketone, to dissolve the obtained polynuclear polyphenol and then cause crystallization or precipitation and filter out the precipitated target, or isolate and refine polynuclear polyphenol by means of column chromatography.

EXAMPLES

The present invention is explained in greater detail below by citing examples.

Reference Example 1

Synthesis of 2,2-bis {4,4-bis(3-formyl-4-hydroxy-5-methylphenyl)cyclohexyl}propane Step 1 Synthesis of 2,2-bis{4,4-bis(4-hydroxy-3-hydroxymethyl-5-methylphenyl)cyclohexyl}propane Into a four-way flask of 5 L in volume, 1020.0 g (4.08 mol) of 16% aqueous sodium hydroxide solution was introduced and the reaction container was purged with nitrogen, after which 538.0 g (0.85 mol) of 2,2-bis{4,4-bis(4-hydroxy-5-methylphenyl)cyclohexyl}propane was added at approx. 35° C. and the mixture was agitated for 1 hour. Next, 947.1 g (11.05 mol) of 35% aqueous formaldehyde solution was added over 2 hours at 25 to 30° C. under agitation to cause reaction. Thereafter, reaction was continued under agitation for 5 hours at 30° C.

When the reaction was complete, the mixture was cooled to 10° C., and then 550.8 g of methylethylketone was dripped over 20 minutes, after which 1280.0 g of methylisobutylketone was added. Thereafter, 661.8 g of 17.5% aqueous hydrochloric acid solution was added to neutralize the mixture, and then the mixture was heated to 30° C. and let stand for 10 minutes, after which the water layer was removed.

Next, 640.0 g of water was added and the mixture was agitated, after which the water layer was removed. In an environment of 45° C. under decompression, 1021.5 g of solvent was removed by distillation from the obtained oil layer, after which 1280.0 g of toluene was added and the mixture was cooled to cause crystals to precipitate. Precipitated crystals were filtered out to obtain 870.2 g of crude crystals.

Thereafter, the obtained crude crystals, 960.0 g of methylethylketone, 1700.0 g of methylisobutylketone and 800 g of water were introduced to a four-way flask of 5 L in volume, and the mixture was heated to 45° C. to dissolve the crystals and then the mixture was let stand to remove the water layer, after which 1470.5 g of solvent was removed by distillation from the obtained oil layer at 45° C. under decompression (crystals precipitated in the middle), followed by cooling to 20° C., filtering, and drying, to obtain 224.8 g of white powder of the target (93.3% pure based on high-speed liquid chromatography). The white powder was confirmed as the target compound by proton NMR analysis. The yield relative to the material tetrakisphenol was 35.1%.

1H-NMR measurement (400 MHz, solvent: DMSO-d6)

[Chemical 51]

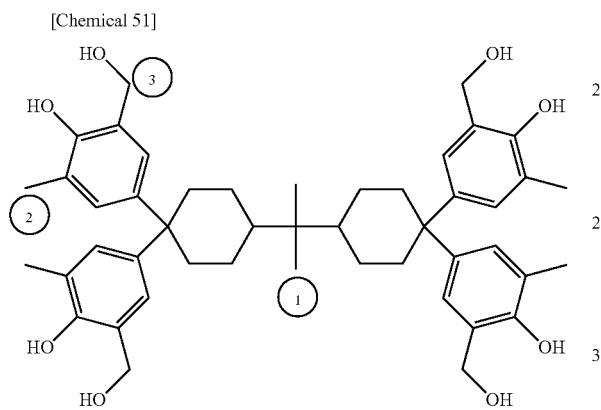

TABLE 1

Identification results by 1H-NMR (400 MHz)
(internal reference: tetramethylsilane)

| Shift value (ppm) | Number of protons | Signal | Assignment |
|---|---|---|---|
| 0.46 | 6 | s | —CH$_3$① |
| 1.05-1.14 | 4 | m | —CH$_2$(cyclohexyl) |
| 1.30-1.36 | 2 | m | —CH(cyclohexyl) |
| 1.51-1.54 | 4 | m | —CH$_2$(cyclohexyl) |
| 1.63-1.69 | 4 | m | —CH$_2$(cyclohexyl) |
| 2.05-2.12 | 12 | m | —CH$_3$② |
| 2.66-2.69 | 4 | m | —CH$_2$(cyclohexyl) |
| 4.45-4.53 | 8 | m | —CH$_2$③ |
| 5.21-5.27 | 4 | m | —OH |
| 6.76-7.03 | 8 | m | Ph—H |
| 8.11-8.15 | 4 | m | Ph—OH |

Step 2 Synthesis of 2,2-bis{4,4-bis(3-formyl-4-hydroxy-5-methylphenyl)cyclohexyl}propane Into a four-way flask of 3 L in volume, 461.7 g (4.05 mol) of trifluoroacetate was introduced and the reaction container was purged with nitrogen, after which 83.3 g (0.594 mol) of hexamethylenetetramine was added at approx. 30° C. and then 101.7 g (0.135 mol) of 2,2-bis {4,4-bis(4-hydroxy-3-hydroxymethyl-5-methylphenyl)cyclohexyl}propane(methylol) obtained in Step 1 was added under agitation over 1 hour 30 minutes at 60° C. to cause reaction. Thereafter, reaction was continued under agitation for 16 hours at 80° C.

To the reaction liquid obtained, 251.5 g of water was added and the mixture was hydrolyzed for 1 hour at 60° C. During the course of hydrolysis, viscous solids precipitated. To this liquid mixture, 201.2 g of toluene and 301.8 g of methylisobutylketone were added and the mixture was heated to 70° C. to dissolve the solids, after which the mixture was let stand and the water layer was removed. Thereafter, 444.8 g of 16% aqueous sodium hydroxide solution was added to neutralize the mixture, and when the mixture was cooled, crystals precipitated. The mixture was cooled further to 20° C., and then the precipitants were filtered out to obtain 104.0 g of crude crystals.

Thereafter, the obtained crude crystals and 1814.0 g of tetrahydrofuran were introduced to a four-way flask of 3 L in volume, and the mixture was heated to 60° C. to dissolve the crystals, after which 1449.0 g of solvent was removed by distillation at normal pressure. Crystals precipitated in the middle. The remaining liquid was mixed with 240.0 g of water and 144.0 g of acetone and then cooled to 20° C., filtered, and dried, to obtain 71.2 g of yellow powder of the target (96.2% pure based on high-speed liquid chromatography). The yellow powder was confirmed as the target compound by proton NMR analysis. The yield relative to the material methylol was 70.8%.

1H-NMR measurement (400 MHz, solvent: DMSO-d6)

[Chemical 52]

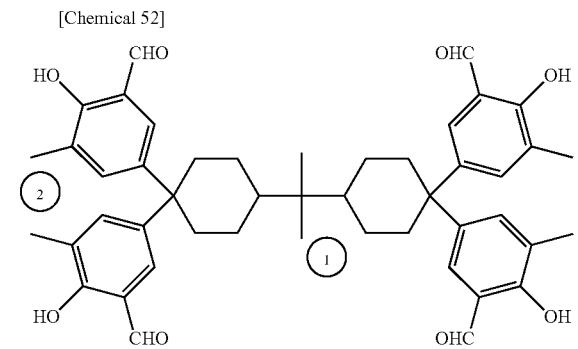

TABLE 2

Identification results by 1H-NMR (400 MHz)
(internal reference: tetramethylsilane)

| Shift value (ppm) | Number of protons | Signal | Assignment |
|---|---|---|---|
| 0.47 | 6 | s | —CH$_3$① |
| 1.05-1.14 | 4 | m | —CH$_2$(cyclohexyl) |
| 1.38-1.43 | 2 | m | —CH(cyclohexyl) |
| 1.59-1.62 | 4 | m | —CH$_2$(cyclohexyl) |
| 1.74-1.77 | 4 | m | —CH$_2$(cyclohexyl) |
| 2.10-2.18 | 12 | m | —CH$_3$② |
| 2.79-2.82 | 4 | m | —CH$_2$(cyclohexyl) |
| 7.34-7.69 | 8 | m | Ph—H |
| 9.97-10.06 | 4 | m | Ph—OH |
| 10.83-10.91 | 4 | m | —CHO |

Example 1

Synthesis of 2,2-bis{4,4-bis(3-formyl-4-methoxycarbonylmethoxy-5-methylphenyl)cyclohexyl}propane Into a four-way flask of 500 mL in volume, 37.2 g (0.05 mol) of 2,2-bis {4,4-bis(3-formyl-4-hydroxy-5-methylphenyl)cyclohexyl}propane obtained in Reference Example 1 and 111.6 g of N-methyl pyrrolidone were introduced and the interior of the flask was purged with nitrogen. This mixture solution was heated to 50° C., and then 5.6 g (0.034 mol) of potassium iodide and 33.1 g (0.24 mol) of potassium carbonate were added and the mixture was agitated for 1 hour. Next, the mixture was heated to 60° C., and then 64.8 g (0.60 mol) of methylchloroacetate was dripped over 1 hour under agitation to cause reaction. Reaction was continued for 3 hours at 60° C. under agitation.

To the reaction liquid, 98.0 g of methylisobutylketone and 147.0 g of water were added and the mixture was agitated and then let stand to remove the water layer, after which 50.0 g of water was added to the oil layer and the mixture was agitated, followed by removal of the water layer. Thereafter, the same operation of water washing and liquid separation was repeated twice. The obtained oil layer was transferred to an evaporator and the solvent was removed by distillation at 60° C. under decompression to obtain 43.7 g of light-yellow powder solids (89.0% pure based on high-speed liquid chromatography). The NMR analysis of the obtained product confirmed that it was indeed the target.

The yield relative to the material 2,2-bis{4,4-bis(3-formyl-4-hydroxy-5-methylphenyl)cyclohexyl}propane(tetraaldehyde) was 84.5%.

1H-NMR analysis (400 MHz, solvent: DMSO-d6)

[Chemical 53]

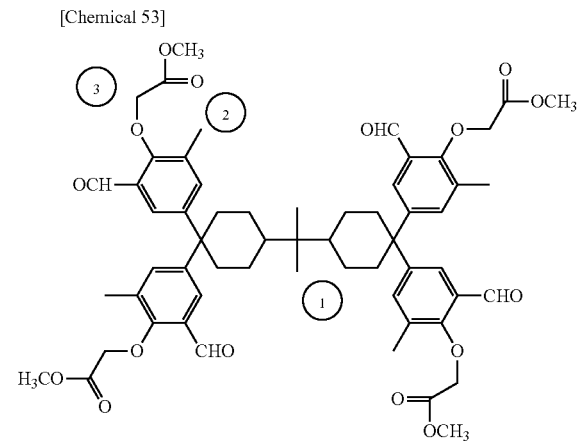

TABLE 3

Identification results by 1H-NMR (400 MHz)
(internal reference: tetramethylsilane)

| Shift value (ppm) | Number of protons | Signal | Assignment |
| --- | --- | --- | --- |
| 0.43 | 6 | s | —CH₃ ① |
| 0.97-1.07 | 4 | m | —CH₂(cyclohexyl) |
| 1.35-1.41 | 2 | m | —CH(cyclohexyl) |
| 1.59-1.61 | 4 | m | —CH₂(cyclohexyl) |
| 1.74-1.81 | 4 | m | —CH₂(cyclohexyl) |
| 2.25-2.31 | 12 | m | —CH₃ ② |
| 2.84-2.87 | 4 | m | —CH₂(cyclohexyl) |
| 3.67-3.68 | 12 | m | —OCH₃ |
| 4.70-4.75 | 8 | m | —CH₂ ③ |
| 7.47-7.65 | 8 | m | Ph—H |
| 10.32-10.38 | 4 | m | —CHO |

Example 2

Synthesis of 2,2-bis[4,4-bis{3-bis(2,5-dimethyl-4-hydroxyphenyl)methyl-4-carboxymethoxy-5-methylphenyl}cyclohexyl]propane Into a four-way flask of 1 L in volume, 48.8 g (0.4 mol) of 2,5-xylenol and 73.2 g of methanol were introduced and the interior of the flask was purged with nitrogen, after which 19.5 g of 35% hydrochloric acid water was added. To the obtained mixture, 39.1 g (0.04 mol) of 2,2-bis{4,4-bis (3-formyl-4-methoxycarbonylmethoxy-5-methylphenyl) cyclohexyl}propane obtained in Example 1 was added over 1.5 hours at 40° C. under agitation to cause reaction. Thereafter, reaction was continued for 17 hours at 50° C. under agitation.

When the reaction was complete, 68.6 g of 25% aqueous tetramethylammonium hydroxide solution was added to neutralize the mixture, and then 150.0 g of methylisobutylketone and 75.0 g of water were added and the mixture was agitated, after which it was let stand at 50° C. and the water layer was removed, and then 75.0 g of water was added further and the same operation of water washing and liquid separation was performed. The obtained oil layer was mixed with 174.7 g of 25% aqueous tetramethylammonium hydroxide solution and the mixture was agitated for 1 hour at 50° C. to cause hydrolysis, after which the hydrolyzed mixture was let stand and the top layer was removed. After the obtained water layer was mixed with 226.0 g of methylisobutylketone at 50° C., 52.6 g of 35% hydrochloric acid water was added to neutralize the mixture, after which it was let stand and the water layer was removed. Further, 100.0 g of water was added and the same operation of water washing and liquid separation was performed at 70° C. The solvent was removed by distillation from the obtained oil layer at 70° C. under decompression, and 75.0 g of acetone was added and mixed. The obtained solution was dripped into 1400 g of toluene at room temperature to cause precipitation. Precipitated solids were then filtered out and dried to obtain 62.4 g of light-yellow powder of the target (87.7% pure based on high-speed liquid chromatography). The NMR analysis of the obtained product confirmed that it was indeed the target. The yield relative to the material 2,2-bis{4,4-bis (3-formyl-4-methoxycarbonylmethoxy-5-methylphenyl) cyclohexyl}propane was 87.3%.

Glass transition temperature (differential scanning calorimetry) 204.9° C.

1H-NMR analysis (400 MHz, solvent: DMSO-d6)

[Chemical 54]

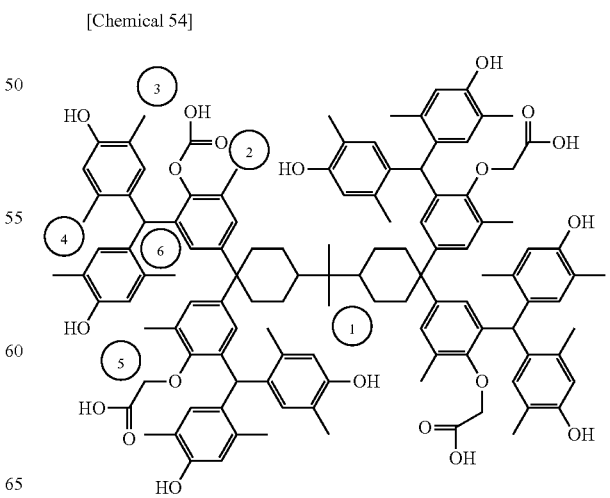

TABLE 4

Identification results by 1H-NMR (400 MHz)
(internal reference: tetramethylsilane)

| Shift value (ppm) | Number of protons | Signal | Assignment |
|---|---|---|---|
| 0.32 | 6 | s | —CH$_3$① |
| 0.60 | 4 | s | —CH$_2$(cyclohexyl) |
| 1.03 | 2 | s | —CH(cyclohexyl) |
| 1.22 | 4 | s | —CH$_2$(cyclohexyl) |
| 1.48 | 4 | s | —CH$_2$(cyclohexyl) |
| 1.67-2.29 | 64 | m | —CH$_2$(cyclohexyl) + —CH$_3$(② + ③ + ④) |
| 3.82-3.85 | 8 | m | —CH$_2$⑤ |
| 5.79-5.80 | 4 | m | —CH⑥ |
| 6.30-7.25 | 24 | m | Ph—H |
| 8.88 | 8 | s | Ph—OH |
| 12.73 | 4 | s | —COOH |

Example 3

Synthesis of 2,2-bis{4,4-bis[3-bis(2,5-dimethyl-4-hydroxyphenyl)methyl-4-(2-methyl-2-adamantyl)oxycarbonylmethoxycarbonylmethoxy-5-methylphenyl]cyclohexyl}propane (Compound 1)

Into a four-way flask of 1 L in volume, 18.1 g (1.5×10$^{-2}$ mol) of 2,2-bis{4,4-bis[3-bis(2,5-dimethyl-4-hydroxyphenyl)methyl-4-carboxymethoxy-5-methylphenyl]cyclohexyl}propane obtained in Example 2 and 45.3 g of N-methyl pyrrolidone were introduced and dissolved at 30° C., and the interior of the flask was purged with nitrogen, after which 7.3 g (7.2×10$^{-2}$ mol) of triethyl amine was added at 35° C. and the mixture was agitated for 30 minutes. Next, 19.4 g (6.75×10$^{-2}$ mol) of 2-methyl-2-adamantyl bromoacetate was added over 1 hour 40 minutes at 35° C. under agitation to cause reaction. Thereafter, reaction was continued for 6 hours at 35° C. under agitation. When the reaction was complete, 61.0 g of toluene and 30.0 g of water were added to the reaction liquid and the liquid was agitated for 10 minutes, after which it was let stand and the bottom layer (water layer) was removed. The obtained oil layer was mixed with 30.0 g of water and the same operation of water washing and liquid separation (removal of water layer) was repeated twice. The solvent was removed by distillation from the obtained oil layer under decompression, thereby concentrating the remaining liquid, after which it was refined by silica gel column chromatography. The obtained fraction containing the target was condensed under decompression to obtain 13.3 g of light-yellowish white powder of the target (95.2% pure based on high-speed liquid chromatography). The NMR analysis of the obtained product confirmed that it was indeed the target. The yield relative to the material carboxylic acid was 43.6%.

1H-NMR analysis (400 MHz, solvent: DMSO-d6, reference substance: tetramethylsilane)

[Chemical 55]

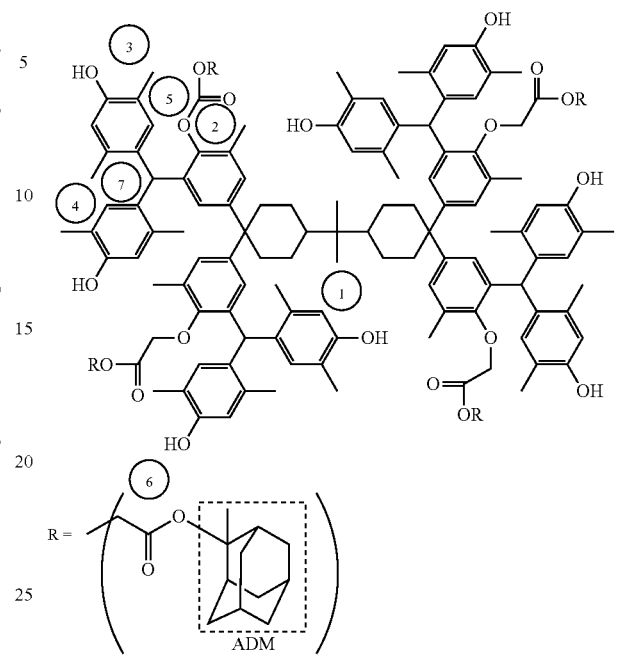

TABLE 5

Identification results by 1H-NMR (400 MHz)

| Shift value (ppm) | Number of protons | Signal | Assignment |
|---|---|---|---|
| 0.31 | 6 | s | —CH$_3$① |
| 0.59 | 4 | s | —CH$_2$(cyclohexyl) |
| 1.03 | 2 | s | —CH(cyclohexyl) |
| 1.22 | 4 | s | —CH$_2$(cyclohexyl) |
| 1.51-2.22 | 136 | m | —CH$_2$(cyclohexyl) + —CH$_3$(② + ③ + ④) ADM |
| 3.97-4.03 | 8 | m | —CH$_2$⑤ |
| 4.62-4.64 | 8 | m | —CH$_2$⑥ |
| 5.72-5.73 | 4 | m | —CH⑦ |
| 6.26-6.94 | 24 | m | Ph—H |
| 8.83-8.91 | 8 | m | Ph—OH |

What is claimed is:
1. A tetrakis(ether-substituted formylphenyl) having General Formula (1) below:

General Formula (1)

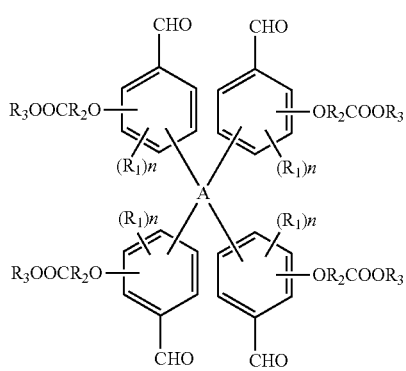

wherein $R_1$ represents an alkyl group with 1 to 8 carbon atoms or alkoxyl group with 1 to 8 carbon atoms, or aromatic hydrocarbon group or saturated hydrocarbon group with 1 to 8 carbon atoms having an aromatic hydrocarbon group, n represents 0 or an integer of 1 to 3, $R_2$ represents a divalent monocyclic or fused-ring aromatic hydrocarbon group with 6 to 15 carbon atoms or divalent aliphatic hydrocarbon group with 1 to 8 carbon atoms that may have a monocyclic or fused-ring aromatic hydrocarbon group with 6 to 15 carbon atoms, $R_3$ represents a hydrogen atom or alkyl group with 1 to 6 carbon atoms, A represents a tetravalent carbon atom group or tetravalent saturated hydrocarbon group with 2 or more carbon atoms, where, if A is a tetravalent saturated hydrocarbon group with 2 or more carbon atoms, the two carbon atoms in the A group are bonded with two phenyl groups, respectively.

* * * * *